United States Patent
Lu et al.

(10) Patent No.: US 6,958,155 B2
(45) Date of Patent: Oct. 25, 2005

(54) COSMETIC COMPOSITIONS COMPRISING AT LEAST ONE POLYSILOXANE BASED POLYAMIDE

(75) Inventors: Shaoxiang Lu, Plainsboro, NJ (US); Wei Yu, Edison, NJ (US); Xavier Blin, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/166,762

(22) Filed: Jun. 12, 2002

(65) Prior Publication Data

US 2004/0001799 A1 Jan. 1, 2004

(51) Int. Cl.⁷ ............................................. A61K 7/48
(52) U.S. Cl. .................... 424/401; 424/59; 424/61; 424/63; 424/64; 424/69; 424/70.1; 424/70.7; 424/78.02
(58) Field of Search .................... 424/401, 59, 61, 424/63, 64, 69, 70.1, 70.7, 78.02

(56) References Cited

U.S. PATENT DOCUMENTS

| | | |
|---|---|---|
| 2,823,195 A | 2/1958 | Shorr et al. |
| 3,723,566 A | 3/1973 | Thompson et al. |
| 4,322,400 A | 3/1982 | Yuhas |
| 5,262,505 A | 11/1993 | Nakashima et al. |
| 5,407,986 A | 4/1995 | Furukawa et al. |
| 5,412,004 A | 5/1995 | Tachibana et al. |
| 5,473,041 A | 12/1995 | Itoh |
| 5,567,428 A | 10/1996 | Hughes |
| 5,837,223 A | 11/1998 | Barone et al. |
| 5,874,069 A | 2/1999 | Mendolia et al. |
| 5,919,441 A | 7/1999 | Mendolia et al. |
| 5,981,680 A | 11/1999 | Petroff et al. |
| 6,051,216 A | 4/2000 | Barr et al. |
| 6,060,072 A | 5/2000 | Konik et al. |
| 6,103,250 A | 8/2000 | Brieva et al. |
| 6,353,076 B1 | 3/2002 | Barr et al. |
| 6,362,287 B1 | 3/2002 | Chorvath et al. |
| 6,362,288 B1 | 3/2002 | Brewer et al. |
| 6,423,324 B1 | 7/2002 | Murphy et al. |
| 6,426,062 B1 | 7/2002 | Chopra et al. |
| 6,451,295 B1 | 9/2002 | Cai et al. |
| 6,503,632 B1 | 1/2003 | Hayashi et al. |
| 6,569,955 B1 | 5/2003 | Brewer et al. |
| 2002/0048557 A1 | 4/2002 | Cai et al. |
| 2003/0068348 A1 | 4/2003 | Ferrari et al. |
| 2003/0072730 A1 | 4/2003 | Tournilhac |
| 2003/0082129 A1 | 5/2003 | Buckingham et al. |
| 2003/0170188 A1 | 9/2003 | Ferrari et al. |

FOREIGN PATENT DOCUMENTS

| | | |
|---|---|---|
| EP | 0 377 447 A2 | 7/1990 |
| EP | 0 693 517 A1 | 1/1996 |
| EP | 0 923 928 | 6/1999 |
| EP | 1 048 686 | 11/2000 |
| EP | 1 068 856 | 1/2001 |
| FR | 2 765 800 | 1/1999 |
| GB | 134 8783 | 3/1974 |
| WO | WO 97/36572 | 10/1997 |
| WO | WO 97/36573 | 10/1997 |
| WO | WO 99/47111 | 1/1999 |
| WO | WO 99/06473 | 2/1999 |
| WO | WO 01/09239 A1 | 2/2001 |
| WO | WO 01/97758 A2 | 12/2001 |
| WO | WO 02/089760 A1 | 11/2002 |
| WO | WO 03/013447 A2 | 2/2003 |
| WO | WO 03/105788 A2 | 6/2003 |

OTHER PUBLICATIONS

Dow Corning® 2–8178 Gellant, Ref. No. 27–1055–01, Aug. 2002, 35 pp.

*Primary Examiner*—Jyothsna A. Venkat
(74) *Attorney, Agent, or Firm*—Oblon, Spivak, McClelland, Maier & Neustadt, P.C.

(57) ABSTRACT

The invention relates to a physiologically acceptable composition, especially a cosmetic composition, comprising at least one volatile solvent and a liquid fatty phase comprising at least one structuring polymer, said structuring polymer (homopolymer or copolymer) having an average molecular weight of from 500 to 500,000 and comprising at least one moiety which comprises:
- at least one polyorganosiloxane group consisting of 1 to 1000 organosiloxane units in the chain of the moiety or in the form of graft and
- at least two groups capable of establishing hydrogen interactions, the polymer being solid at room temperature and soluble in the liquid fatty phase at a temperature of from 25 to 250° C.

25 Claims, No Drawings

COSMETIC COMPOSITIONS COMPRISING AT LEAST ONE POLYSILOXANE BASED POLYAMIDE

The present invention relates to a composition, in one embodiment a transfer resistant cosmetic composition, which may also be pliable and/or comfortable to wear upon application to a keratinous substrate. The composition comprises, more particularly, at least one liquid fatty phase structured by a structuring polymer and at least one volatile solvent. The invention, in one embodiment, relates to cosmetic, dermatological, and pharmaceutical products containing this composition. As used herein, the expression "at least one" means one or more and thus includes individual components as well as mixtures/combinations.

Many cosmetic compositions, including pigmented cosmetics such as foundations, concealers, lipsticks, mascaras, and other cosmetic and sunscreen compositions, have been developed for longer wear and transfer resistance properties. This is accomplished by the use of compositions that form a film after application. Such compositions generally contain volatile solvents, which evaporate on contact with the skin or other keratinous tissue, leaving behind a layer comprising waxes and/or resins, pigments, fillers, and actives. However, these compositions tend to be uncomfortable for the wearer as the composition remains on the skin or other keratinous tissue as a brittle or non-flexible film. Such compositions may not be either pliable or soft, and they may not be comfortable to wear. There may also be a tendency for such compositions to flake off because of poor adherence to the skin or other keratinous tissue. Furthermore, compositions may have a tendency to be tacky, resulting in poor application and spreadability characteristics.

The need therefore still remains for improved long-wearing cosmetic compositions which transfer little or not at all, i.e., "transfer-free" or transfer resistant compositions which also possess good cosmetic properties such as pliability and comfort. For example, a composition that is transfer resistant may deposit a film onto a keratinous substance that may not transfer when the keratinous substance comes into contact with, for example, skin, clothes, a cup, paper, cigarette, or a handkerchief.

To achieve at least one of these and other advantages, the present invention, in one aspect, provides a composition comprising at least one volatile solvent and a liquid fatty phase comprising at least one structuring polymer, said structuring polymer (homopolymer or copolymer) having an average molecular weight of from 500 to 500,000 and comprising at least one moiety which comprises:

at least one polyorganosiloxane group consisting of 1 to 1000 organosiloxane units in the chain of the moiety or in the form of graft and
  at least two groups capable of establishing hydrogen interactions, chosen from ester, amide, sulphonamide, carbamate, thiocarbamate, urea and thiourea groups, and combinations thereof, on condition that at least one of the groups is other than an ester group, the polymer being solid at room temperature and soluble in the liquid fatty phase at a temperature of from 25 to 250° C. The present invention also relates to a method for making such a composition.

Another aspect of the invention provides a cosmetic make up composition for keratinous substances, such as skin, hair, eye lashes, eye brows, nails, lips, comprising at least one volatile solvent and a liquid fatty phase comprising at least one structuring polymer, said structuring polymer (homopolymer or copolymer) having an average molecular weight of from 500 to 500,000 and comprising at least one moiety which comprises:

at least one polyorganosiloxane group consisting of 1 to 1000 organosiloxane units in the chain of the moiety or in the form of graft and
  at least two groups capable of establishing hydrogen interactions, chosen from ester, amide, sulphonamide, carbamate, thiocarbamate, urea and thiourea groups, and combinations thereof, on condition that at least one of the groups is other than an ester group, the polymer being solid at room temperature and soluble in the liquid fatty phase at a temperature of from 25 to 250° C. The present invention also relates to a method for making such a composition.

Another aspect of the invention provides a cosmetic stick composition for keratinous substances, such as skin, hair, eye lashes, eye brows, nails, lips, comprising pigments and at least one volatile solvent and a liquid fatty phase comprising at least one structuring polymer, said structuring polymer (homopolymer or copolymer) having an average molecular weight of from 500 to 500,000 and comprising at least one moiety which comprises:

at least one polyorganosiloxane group consisting of 1 to 1000 organosiloxane units in the chain of the moiety or in the form of graft and
  at least two groups capable of establishing hydrogen interactions, chosen from ester, amide, sulphonamide, carbamate, thiocarbamate, urea and thiourea groups, and combinations thereof, on condition that at least one of the groups is other than an ester group, the polymer being solid at room temperature and soluble in the liquid fatty phase at a temperature of from 25 to 250° C. The present invention also relates to a method for making such a composition.

It is to be understood that both the foregoing general description and the following detailed description are exemplary and explanatory only, and are not restrictive of the invention.

By transfer resistant compositions, we mean compositions which transfer little or not at all, i.e., "transfer-free" or transfer resistant compositions. For example, a composition that is transfer resistant may deposit a film onto a keratinous substance that may not transfer when the keratinous substance comes into contact with, for example, skin, clothes, a cup, paper, cigarette, or a handkerchief.

In one embodiment, the liquid phase comprising at least one structuring polymer and the at least one volatile solvent are present in an amount effective to provide transfer resistant properties, and may also provide at least one of the following properties: pliability, softness, and wearing comfort.

For example, the composition of the present invention may be in a form chosen from a paste, a solid, a gel, and a cream. It may be an emulsion, such as an oil-in-water or water-in-oil emulsion, a multiple emulsion, such as an oil-in-water-in-oil emulsion or a water-in-oil-in-water emulsion, or a solid, rigid or supple gel, including anhydrous gels. In one embodiment, the composition of the invention is anhydrous. The composition of the invention may, for example, comprise an external or continuous fatty phase. In another embodiment, the composition of the invention is transparent or clear, including for example, a composition without pigments. The composition can also be in a form chosen from a translucent anhydrous gel and a transparent anhydrous gel. The composition can also be a molded composition or cast as a stick or a dish. The composition in one embodiment is a solid such as a molded stick or a poured stick.

The structuring of the liquid fatty phase is controlled by the type of structuring polymer used and is such that a rigid structure in the form of a stick, of good mechanical resistance, is obtained. These rigid compositions, when colored, allow for a supple, light, non-transfer, non-migrating and long-wearing applications on a keratinous surface. The composition may contain one or more structuring polymers.

The inventive, structured compositions may be in the form a foundation or a mascara, which exhibit excellent and improved properties of non-transfer, flexibility and pliability.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 40° C., 37° C., 45° C., 50° C. and under freeze-thaw conditions. A composition is considered to lack stability if in any of these tests an abnormality that impedes functioning of the composition is observed. The skilled artisan will readily recognize an abnormality that impedes functioning of a composition based on the intended application.

The Volatile Solvent

According to the invention, the volatile silicone oil may be selected from the group consisting of linear or cyclic silicones having a flash point of at least 40° C., such as linear or cyclic polydimethylsiloxanes.

Non-limiting examples of such volatile oils are given in Table 1 below.

TABLE 1

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3 St) from Dow Corning | 102 | 3 |

According to the invention the non-silicone volatile oils may be selected from the group of volatile hydrocarbon oils, volatile esters and volatile ethers. This includes, but is not limited to, volatile hydrocarbons, such as isododecane and isohexadecane, $C_8$–$C_{16}$ isoparaffins, isohexyl or isodecyl neopentanoates and their mixtures.

Non-limiting examples of such volatile oils are given in Table 2 below.

TABLE 2

| Compound | Flash Point (° C.) |
| --- | --- |
| Isododecane | 43 |
| Isohexadecane | 102 |
| Isodecyl Neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$–$C_{13}$) | 62 |
| Isopar H (isoparaffin $C_{11}$–$C_{12}$) | 56 |

According to the invention, these volatile oils permit an easier application of the composition on the skin, lips or keratinous fibers. These oils may be hydrocarbon oils, silicone oils optionally substituted with pendant or terminal alkyl or alkoxy groups, or a mixture of these oils.

Non limiting examples of volatile oils that may be used according to the invention are linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C.

Other volatile oils usable in this invention may also include volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl neopentanoate and their mixtures. In another embodiment, the invention comprises at least one volatile silicone oil having a flash point above 40° C.

The Structuring Polymer

The polymers used as gelling agents in the composition of the invention are polymers of the polyorganosiloxane type such as those described in documents U.S. Pat. Nos. 5,874,069, 5,919,441, 6,051,216 and 5,981,680.

According to the invention, the polymers used as gelling agent may belong to the following two families:

a) polyorganosiloxanes comprising at least two groups capable of establishing hydrogen interactions, these two groups being located in the polymer chain; and/or b) polyorganosiloxanes comprising at least two groups capable of establishing hydrogen interactions, these two groups being located on grafts or branches.

The polymers to which the invention applies are solids that may be dissolved beforehand in a solvent with hydrogen interaction capable of breaking the hydrogen interactions of the polymers, for instance $C_2$ to $C_8$ lower alcohols and especially ethanol, n-propanol or isopropanol, before being placed in the presence of the silicone oils according to the invention. It is also possible to use these hydrogen interaction "breaking" solvents as co-solvents. These solvents may then be stored in the composition or may be removed by selective evaporation, which is well known to those skilled in the art.

The polymers comprising two groups capable of establishing hydrogen interactions in the polymer chain may be polymers comprising at least one moiety corresponding to the formula:

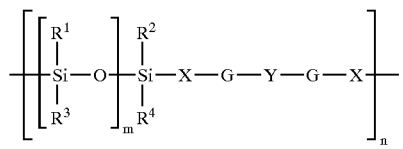

in which:

1) $R^1$, $R^2$, $R^3$ and $R^4$, which may be identical or different, represent a group chosen from:

linear, branched or cyclic, saturated or unsaturated, $C_1$ to $C_{40}$ hydrocarbon-based groups, possibly containing in their chain one or more oxygen, sulphur and/or nitrogen atoms, and possibly being partially or totally substituted with fluorine atoms, $C_6$ to $C_{10}$ aryl groups, optionally substituted with one or more $C_1$ to $C_4$ alkyl groups, polyorganosiloxane chains possibly containing one or more oxygen, sulphur and/or nitrogen atoms;

2) the groups X, which may be identical or different, represent a linear or branched $C_1$ to $C_{30}$ alkylenediyl group, possibly containing in its chain one or more oxygen and/or nitrogen atoms;

3) Y is a saturated or unsaturated, $C_1$ to $C_{50}$ linear or branched divalent alkylene, arylene, cycloalkylene, alkylarylene or arylalkylene group, possibly comprising one or more oxygen, sulphur and/or nitrogen atoms, and/or bearing as substituent one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or 4) Y represents a group corresponding to the formula:

in which

T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and $R^5$ represents a linear or branched $C_1$ to $C_{50}$ alkyl group or a polyorganosiloxane chain, possibly comprising one or more ester, amide, urethane, thiocarbamate, urea, thiourea and/or sulphonamide groups, which may be linked to another chain of the polymer;

5) the groups G, which may be identical or different, represent divalent groups chosen from:

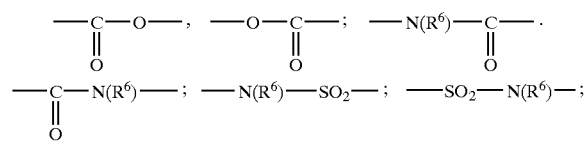

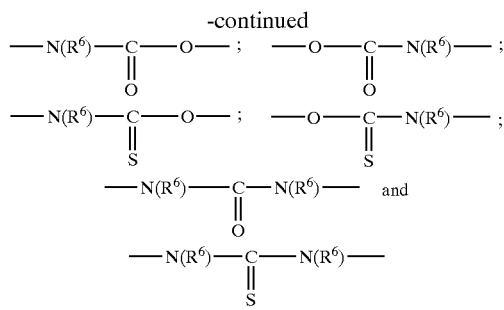

in which $R^6$ represents a hydrogen atom or a linear or branched $C_1$ to $C_{20}$ alkyl group, on condition that at least 50% of the groups $R^6$ of the polymer represents a hydrogen atom and that at least two of the groups G of the polymer are a group other than:

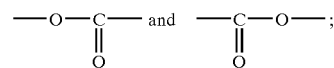

6) n is an integer ranging from 2 to 500 and preferably from 2 to 200, and m is an integer ranging from 1 to 1000, preferably from 1 to 700 and better still from 6 to 200.

According to the invention, 80% of the groups $R^1$, $R^2$, $R^3$ and $R^4$ of the polymer are preferably chosen from methyl, ethyl, phenyl and 3,3,3-trifluoropropyl groups.

According to the invention, Y can represent various divalent groups, furthermore optionally comprising one or two free valencies to establish bonds with other moieties of the polymer or copolymer. Preferably, Y represents a group chosen from:

a) linear $C_1$ to $C_{20}$ and preferably $C_1$ to $C_{10}$ alkylene groups, b) $C_{30}$ to $C_{56}$ branched alkylene groups possibly comprising rings and unconjugated unsaturations, c) $C_5$–$C_6$ cycloalkylene groups, d) phenylene groups optionally substituted with one or more $C_1$ to $C_{40}$ alkyl groups, e) $C_1$ to $C_{20}$ alkylene groups comprising from 1 to 5 amide groups, f) $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups, g) polyorganosiloxane chains of formula:

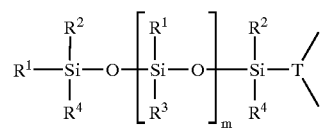

in which $R^1$, $R^2$, $R^3$, $R^4$, T and m are as defined above, and h) polyorganosiloxane chains of formula:

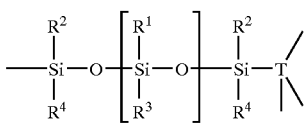

The polyorganosiloxanes of the second family may be polymers comprising at least one moiety corresponding to formula (II):

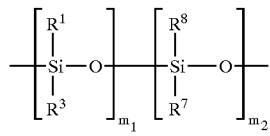

(II)

in which
- $R^1$ and $R^3$, which may be identical or different, are as defined above for formula (I),
- $R^7$ represents a group as defined above for $R^1$ and $R^3$, or represents a group of formula —X-G-$R^9$ in which X and G are as defined above for formula (I) and $R^9$ represents a hydrogen atom or a linear, branched or cyclic, saturated or unsaturated, $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups,
- $R^8$ represents a group of formula —X-G-$R^9$ in which X, G and $R^9$ are as defined above,
- $m_1$ is an integer ranging from 1 to 998, and
- $m_2$ is an integer ranging from 2 to 500.

According to the invention, the polymer used as gelling agent may be a homopolymer, that is to say a polymer comprising several identical moieties, in particular moieties of formula (I) or of formula (II).

According to the invention, it is also possible to use a polymer consisting of a copolymer comprising several different moieties of formula (I), that is to say a polymer in which at least one of the groups $R^1$, $R^2$, $R^3$, $R^4$, X, G, Y, m and n is different in one of the moieties. The copolymer may also be formed from several moieties of formula (II), in which at least one of the groups $R^1$, $R^3$, $R^7$, $R^8$, $m_1$ and $m_2$ is different in at least one of the moieties.

It is also possible to use a copolymer comprising at least one moiety of formula (I) and at least one moiety of formula (II), the moieties of formula (I) and the moieties of formula (II) possibly being identical to or different from each other.

According to one variant of the invention, it is also possible to use a copolymer furthermore comprising at least one hydrocarbon-based moiety comprising two groups capable of establishing hydrogen interactions, chosen from ester, amide, sulphonamide, carbamate, thiocarbamate, urea and thiourea groups, and combinations thereof.

These copolymers may be block copolymers or grafted copolymers.

According to a first embodiment of the invention, the groups capable of establishing hydrogen interactions are amide groups of formulae —C(O)NH— and —HN—C(O)—.

In this case, the gelling agent may be a polymer comprising at least one moiety of formula (III) or (IV):

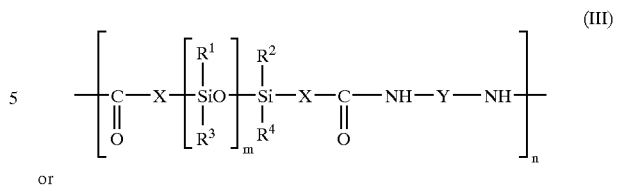

or

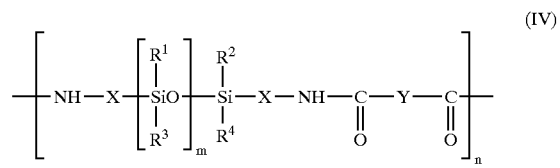

in which $R^1$, $R^2$, $R^3$, $R^4$, X, Y, m and n are as defined above.

Such a moiety may be obtained:

either by a condensation reaction between a silicone containing α,ω-carboxylic acid ends and one or more diamines, according to the following reaction scheme:

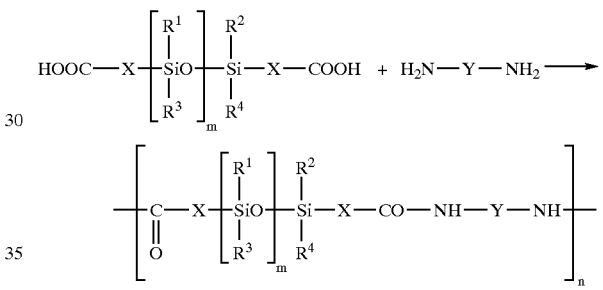

or by reaction of two molecules of α-unsaturated carboxylic acid with a diamine according to the following reaction scheme:

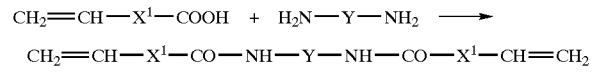

followed by the addition of a siloxane to the ethylenic unsaturations, according to the following scheme:

$$CH_2=CH-X^1-CO-NH-Y-NH-CO-X^1-CH=CH_2$$

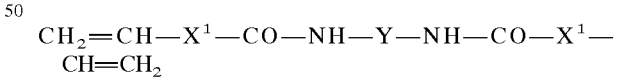

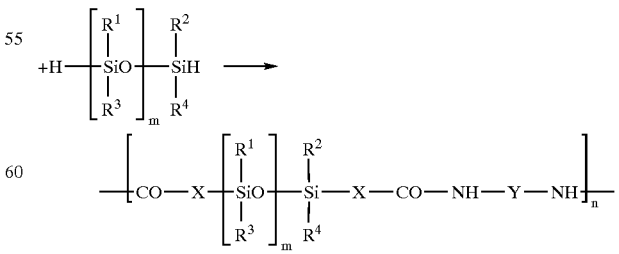

in which $X^1$—$(CH_2)_2$— corresponds to X defined above and Y, $R^1$, $R^2$, $R^3$, $R^4$ and m are as defined above;

or by reaction of a silicone containing α,ω-$NH_2$ ends and a diacid of formula HOOC—Y—COOH according to the following reaction scheme:

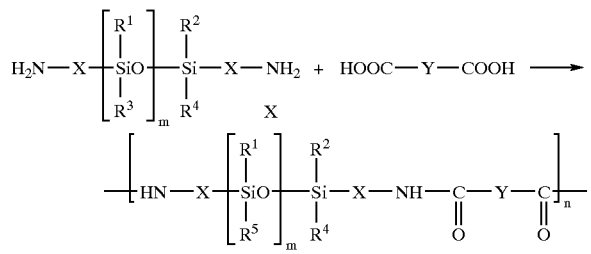

In these polyamides of formula (III) or (IV), m is preferably in the range from 1 to 700, more preferably from 15 to 500 and better still from 15 to 45, and n is in particular in the range from 1 to 500, preferably from 1 to 100 and better still from 4 to 25, X is preferably a linear or branched alkylene chain containing from 1 to 30 carbon atoms and in particular 3 to 10 carbon atoms, and Y is preferably an alkylene chain that is linear or branched or that possibly comprises rings and/or unsaturations, containing from 1 to 40 carbon atoms, in particular from 1 to 20 carbon atoms and better still from 2 to 6 carbon atoms, in particular 6 carbon atoms.

In formulae (III) and (IV), the alkylene group representing X or Y can optionally contain in its alkylene portion at least one of the following elements:

1) 1 to 5 amide, urea or carbamate groups,
2) a $C_5$ or $C_6$ cycloalkyl group, and
3) a phenylene group optionally substituted with 1 to 3 identical or different $C_1$ to $C_3$ alkyl groups.

In formulae (III) and (IV), the alkylene groups may also be substituted with at least one element chosen from the group consisting of:

a hydroxyl group,
a $C_3$ to $C_8$ cycloalkyl group,
one to three $C_1$ to $C_{40}$ alkyl groups,
a phenyl group optionally substituted with one to three $C_1$ to $C_3$ alkyl groups,
a $C_1$ to $C_3$ hydroxyalkyl group, and
a $C_1$ to $C_6$ aminoalkyl group.

In these formulae (III) and (IV), Y may also represent:

in which $R^5$ represents a polyorganosiloxane chain and T represents a group of formula:

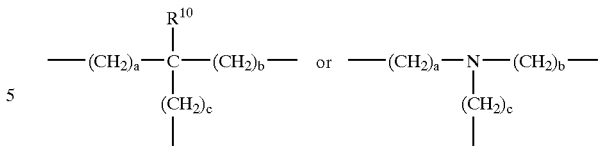

in which a, b and c are, independently, integers ranging from 1 to 10, and $R^{10}$ is a hydrogen atom or a group such as those defined for $R^1$, $R^2$, $R^3$ and $R^4$.

In formulae (III) and (IV), $R^1$, $R^2$, $R^3$ and $R^4$ preferably represent, independently, a linear or branched $C_1$ to $C_{40}$ alkyl group, preferably a $CH_3$, $C_2H_5$, n-$C_3H_7$ or isopropyl group, a polyorganosiloxane chain or a phenyl group optionally substituted with one to three methyl or ethyl groups.

As has been seen previously, the polymer may comprise identical or different moieties of formula (III) or (IV).

Thus, the polymer may be a polyamide containing several moieties of formula (III) or (IV) of different lengths, i.e. a polyamide corresponding to the formula:

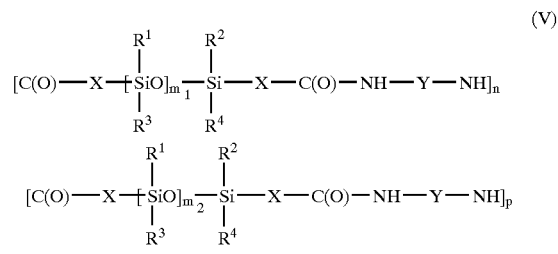

in which X, Y, n and $R^1$ to $R^4$ have the meanings given above, $m_1$ and $m_2$, which are different, are chosen in the range from 1 to 1000, and p is an integer ranging from 2 to 300.

In this formula, the moieties may be structured to form either a block copolymer, or a random copolymer or an alternating copolymer. In this copolymer, the moieties may be not only of different lengths, but also of different chemical structures, for example containing different groups Y. In this case, the copolymer may correspond to the formula:

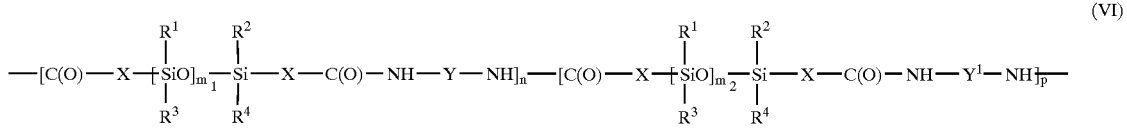

in which $R^1$ to $R^4$, X, Y, $m_1$, $m_2$, n and p have the meanings given above and $Y^1$ is different from Y but chosen from the groups defined for Y. As previously, the various moieties may be structured to form either a block copolymer, or a random copolymer or an alternating copolymer.

In an embodiment of the invention, the gelling agent may also consist of a grafted copolymer. Thus, the polyamide containing silicone units may be grafted and optionally crosslinked with silicone chains containing amide groups. Such polymers may be synthesized with trifunctional amines.

In this case, the copolymer may comprise at least one moiety of formula:

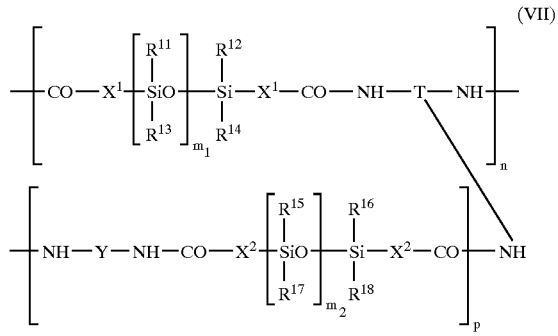

in which $X^1$ and $X^2$, which may be identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are numbers in the range from 1 to 1000, and p is an integer ranging from 2 to 500.

In formula (VII), it is preferred that:
p is in the range from 1 to 25 and better still from 1 to 7, $R^{11}$ to $R^{18}$ are methyl groups,
T corresponds to one of the following formulae:

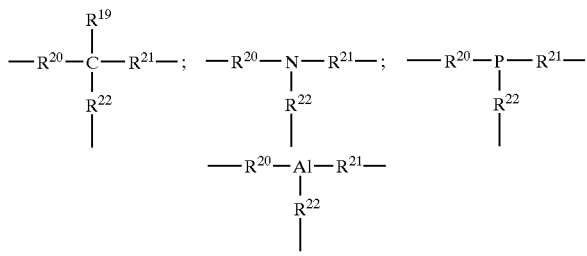

in which $R^{19}$ is a hydrogen atom or a group chosen from the groups defined for $R^1$ to $R^4$, and $R^{20}$, $R^{21}$ and $R^{22}$ are, independently, linear or branched alkylene groups, and more preferably corresponds to the formula:

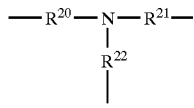

in particular with $R^{20}$, $R^{21}$ and $R^{22}$ representing —$CH_2$—$CH_2$—,
$m_1$ and $m_2$ are in the range from 15 to 500 and better still from 15 to 45,
$X^1$ and $X^2$ represent —$(CH_2)_{10}$—, and
Y represents —$CH_2$—.

These polyamides containing a grafted silicone moiety of formula (VII) may be copolymerized with polyamide-silicones of formula (II) to form block copolymers, alternating copolymers or random copolymers. The weight percentage of grafted silicone moieties (VII) in the copolymer may range from 0.5% to 30% by weight.

According to the invention, as has been seen previously, the siloxane units may be in the main chain or backbone of the polymer, but they may also be present in grafted or pendent chains. In the main chain, the siloxane units may be in the form of segments as described above. In the pendent or grafted chains, the siloxane units may appear individually or in segments.

According to the invention, the preferred siloxane-based polyamides are:
polyamides of formula (III) in which m is from 15 to 50;
mixtures of two or more polyamides in which at least one polyamide has a value of m in the range from 15 to 50 and at least one polyamide has a value of m in the range from 30 to 50;
polymers of formula (V) with $m_1$ chosen in the range from 15 to 50 and $m_2$ chosen in the range from 30 to 500 with the portion corresponding to $m_1$ representing 1% to 99% by weight of the total weight of the polyamide and the corresponding portion $m_2$ representing 1% to 99% by weight of the total weight of the polyamide;
mixtures of polyamide of formula (III) combining
1) 80% to 99% by weight of a polyamide in which n is equal to 2 to 10 and in particular 3 to 6, and
2) 1% to 20% of a polyamide in which n is in the range from 5 to 500 and in particular from 6 to 100;
polyamides corresponding to formula (VI) in which at least one of the groups Y and $Y^1$ contains at least one hydroxyl substituent;
polyamides of formula (III) synthesized with at least one portion of an activated diacid (diacid chloride, dianhydride or diester) instead of the diacid;
polyamides of formula (III) in which X represents —$(CH_2)_3$— or —$(CH_2)_{10}$; and
polyamides of formula (III) in which the polyamides end with a monofunctional chain chosen from the group consisting of monofunctional amines, monofunctional acids, monofunctional alcohols, including fatty acids, fatty alcohols and fatty amines, such as, for example, octylamine, octanol, stearic acid and stearyl alcohol.

According to the invention, the end groups of the polymer chain may end with:
a $C_1$ to $C_{50}$ alkyl ester group by introducing a $C_1$ to $C_{50}$ monoalcohol during the synthesis,
a $C_1$ to $C_{50}$ alkylamide group by taking as stopping group a monoacid if the silicone is α,ω-diaminated, or a monoamine if the silicone is an α,ω-dicarboxylic acid.

According to one embodiment variant of the invention, it is possible to use a copolymer of silicone polyamide and of hydrocarbon-based polyamide, i.e. a copolymer comprising moieties of formula (III) or (IV) and hydrocarbon-based polyamide moieties. In this case, the polyamide-silicone moieties may be arranged at the ends of the hydrocarbon-based polyamide.

Polyamide-based gelling agents containing silicones may be produced by silylic amidation of polyamides based on fatty acid dimer. This approach involves the reaction of free acid sites existing on a polyamide as end sites, with organosiloxane-monoamines and/or organosiloxane-diamines (amidation reaction), or alternatively with oligosiloxane alcohols or oligosiloxane diols (esterification reaction). The esterification reaction requires the presence of acid catalysts, as is known in the art. It is desirable for the polyamide containing free acid sites, used for the amidation or esterification reaction, to have a relatively high number of acid end groups (for example polyamides with high acid numbers, for example from 15 to 20).

For the amidation of the free acid sites of the hydrocarbon-based polyamides, siloxane diamines with 1 to 300, more particularly 2 to 50 and better still 2, 6, 9.5, 12, 13.5, 23 or 31 siloxane groups, may be used for the reaction with hydrocarbon-based polyamides based on fatty acid dimers. Siloxane diamines containing 13.5 siloxane groups are preferred, and the best results are obtained with the siloxane diamine containing 13.5 siloxane groups and polyamides containing high numbers of carboxylic acid end groups.

The reactions may be carried out in xylene to extract the water produced from the solution by azeotropic distillation, or at higher temperatures (about 180 to 200° C.) without solvent. Typically, the efficacy of the amidation and the reaction rates decrease when the siloxane diamine is longer, that is to say when the number of siloxane groups is higher. Free amine sites may be blocked after the initial amidation reaction of the diaminosiloxanes by reacting them either with a siloxane acid, or with an organic acid such as benzoic acid.

For the esterification of the free acid sites on the polyamides, this may be performed in boiling xylene with about 1% by weight, relative to the total weight of the reagents, of para-toluenesulphonic acid as catalyst.

These reactions carried out on the carboxylic acid end groups of the polyamide lead to the incorporation of silicone moieties only at the ends of the polymer chain.

It is also possible to prepare a copolymer of polyamide-silicone, using a polyamide containing free amine groups, by amidation reaction with a siloxane containing an acid group.

It is also possible to prepare a gelling agent based on a copolymer between a hydrocarbon-based polyamide and a silicone polyamide, by transamidation of a polyamide having, for example, an ethylene-diamine constituent, with an oligosiloxane-α,ω-diamine, at high temperature (for example 200 to 300° C.), to carry out a transamidation such that the ethylenediamine component of the original polyamide is replaced with the oligosiloxane diamine.

The copolymer of hydrocarbon-based polyamide and of polyamide-silicone may also be a grafted copolymer comprising a hydrocarbon-based polyamide backbone with pendent oligosiloxane groups.

This may be obtained, for example:

by hydrosilylation of unsaturated bonds in polyamides based on fatty acid dimers;

by silylation of the amide groups of a polyamide; or by silylation of unsaturated polyamides by means of an oxidation, that is to say by oxidizing the unsaturated groups into alcohols or diols, to form hydroxyl groups that are reacted with siloxane carboxylic acids or siloxane alcohols. The olefinic sites of the unsaturated polyamides may also be epoxidized and the epoxy groups may then be reacted with siloxane amines or siloxane alcohols.

According to another embodiment of the invention, the gelling agent consists of a homopolymer or a copolymer comprising urethane or urea groups.

As previously, the polymer may comprise polyorganosiloxane moieties containing two or more urethane and/or urea groups, either in the backbone of the polymer or on side chains or as pendent groups.

The polymers comprising at least two urethane and/or urea groups in the backbone may be polymers comprising at least one moiety corresponding to the following formula:

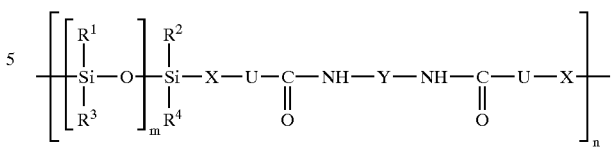

in which $R^1$, $R^2$, $R^3$, $R^4$, X, Y, m and n have the meanings given above for formula (I), and U represents —O— or —NH—, such that:

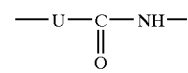

corresponds to a urethane or urea group.

In this formula (VIII), Y may be a linear or branched $C_1$ to $C_{40}$ alkylene group, optionally substituted with a $C_1$ to $C_{15}$ alkyl group or a $C_5$ to $C_{10}$ aryl group. Preferably, a —$(CH_2)_6$— group is used.

Y may also represent a $C_5$ to $C_{12}$ cycloaliphatic or aromatic group that may be substituted with a $C_1$ to $C_{15}$ alkyl group or a $C_5$ to $C_{10}$ aryl group, for example a radical chosen from the methylene-4,4-biscyclohexyl radical, the radical derived from isophorone diisocyanate, 2,4- and 2,6-tolylenes, 1,5-naphthylene, p-phenylene and 4,4'-biphenylenemethane. Generally, it is preferred for Y to represent a linear or branched $C_1$ to $C_{40}$ alkylene radical or a $C_4$ to $C_{12}$ cycloalkylene radical.

Y may also represent a polyurethane or polyurea block corresponding to the condensation of several diisocyanate molecules with one or more molecules of coupling agents of the diol or diamine type. In this case, Y comprises several urethane or urea groups in the alkylene chain.

It may correspond to the formula:

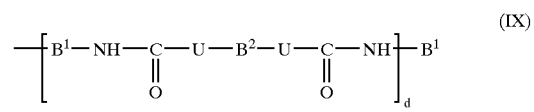

in which $B^1$ is a group chosen from the groups given above for Y, U is —O— or —NH— and $B^2$ is chosen from:

linear or branched $C_1$ to $C_{40}$ alkylene groups, which can optionally bear an ionizable group such as a carboxylic acid or sulphonic acid group, or a neutralizable or quaternizable tertiary amine group, $C_5$ to $C_{12}$ cycloalkylene groups, optionally bearing alkyl substituents, for example one to three methyl or ethyl groups, or alkylene, for example the diol radical: cyclohexanedimethanol, phenylene groups that may optionally bear $C_1$ to $C_3$ alkyl substituents, and groups of formula:

in which T is a hydrocarbon-based trivalent radical possibly containing one or more hetero atoms such as oxygen, sulphur and nitrogen and $R^5$ is a polyorganosiloxane chain or a linear or branched $C_1$ to $C_{50}$ alkyl chain.

T can represent, for example:

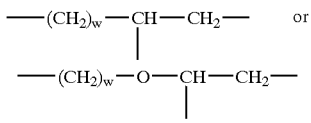

with w being an integer ranging from 1 to 10 and $R^5$ being a polyorganosiloxane chain.

When Y is a linear or branched $C_1$ to $C_{40}$ alkylene group, the $-(CH_2)_2-$ and $-(CH_2)_6-$ groups are preferred.

In the formula given above for Y, d may be an integer ranging from 0 to 5, preferably from 0 to 3 and more preferably equal to 1 or 2.

Preferably, $B^2$ is a linear or branched $C_1$ to $C_{40}$ alkylene group, in particular $-(CH_2)_2-$ or $-(CH_2)_6-$ or a group:

with $R^5$ being a polyorganosiloxane chain.

As previously discussed, the polymer constituting the gelling agent may be formed from silicone urethane and/or silicone urea moieties of different length and/or constitution, and may be in the form of block or random copolymers.

According to the invention, the silicone may also comprise urethane and/or urea groups no longer in the backbone but as side branches.

In this case, the polymer may comprise at least one moiety of formula:

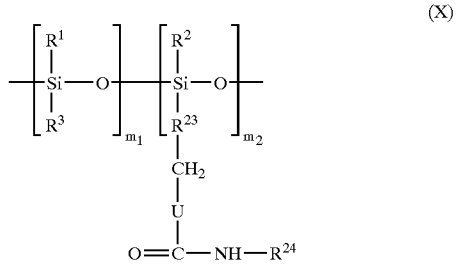

(X)

in which $R^1$, $R^2$, $R^3$, $m_1$ and $m_2$ have the meanings given above for formula (I), U represents O or NH, $R^{23}$ represents a $C_1$ to $C_{40}$ alkylene group, optionally comprising one or more hetero atoms chosen from O and N, or a phenylene group, and $R^{24}$ is chosen from linear, branched or cyclic, saturated or unsaturated $C_1$ to $C_{50}$ alkyl groups, and phenyl groups optionally substituted with one to three $C_1$ to $C_3$ alkyl groups.

The polymers comprising at least one moiety of formula (X) contain siloxane units and urea or urethane groups, and they may be used as gelling agents in the compositions of the invention.

The siloxane polymers may have a single urea or urethane group by branching or may have branches containing two urea or urethane groups, or alternatively they may contain a mixture of branches containing one urea or urethane group and branches containing two urea or urethane groups.

They may be obtained from branched polysiloxanes, comprising one or two amino groups by branching, by reacting these polysiloxanes with monoisocyanates.

As examples of starting polymers of this type containing amino and diamino branches, mention may be made of the polymers corresponding to the following formulae:

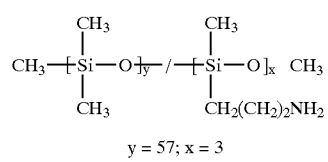

y = 57; x = 3

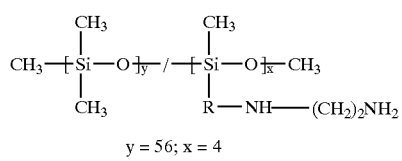

y = 56; x = 4

In these formulae, the symbol "/" indicates that the segments may be of different lengths and in a random order, and R represents a linear aliphatic group preferably containing 1 to 6 carbon atoms and better still 1 to 3 carbon atoms.

Such polymers containing branching may be formed by reacting a siloxane polymer, containing at least three amino groups per polymer molecule, with a compound containing only one monofunctional group (for example an acid, an isocyanate or an isothiocyanate) to react this monofunctional group with one of the amino groups and to form groups capable of establishing hydrogen interactions. The amino groups may be on side chains extending from the main chain of the siloxane polymer, such that the groups capable of establishing hydrogen interactions are formed on these side chains, or alternatively the amino groups may be at the ends of the main chain, such that the groups capable of hydrogen interaction will be end groups of the polymer.

As a procedure for forming a polymer containing siloxane units and groups capable of establishing hydrogen interactions, mention may be made-of the reaction of a siloxane diamine and of a diisocyanate in a silicone solvent so as to provide a gel directly. The reaction may be performed in a silicone fluid, the resulting product being dissolved in the silicone fluid, at high temperature, the temperature of the system then being reduced to form the gel.

The polymers that are preferred for incorporation into the compositions according to the present invention are siloxane-urea copolymers that are linear and that contain urea groups as groups capable of establishing hydrogen interactions in the backbone of the polymer.

As an illustration of a polysiloxane ending with four urea groups, mention may be made of the polymer of formula:

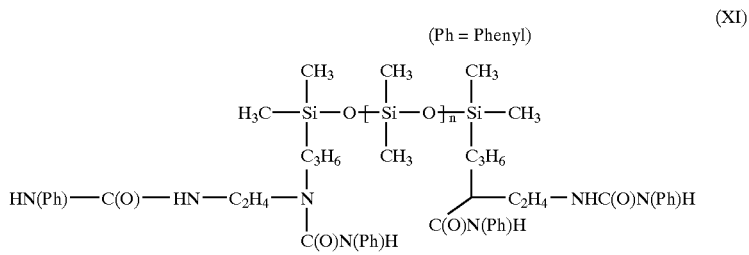

(Ph = Phenyl)

in which Ph is a phenyl group and n is a number from 0 to 300, in particular from 0 to 100, for example 50.

This polymer is obtained by reacting the following polysiloxane containing amino groups:

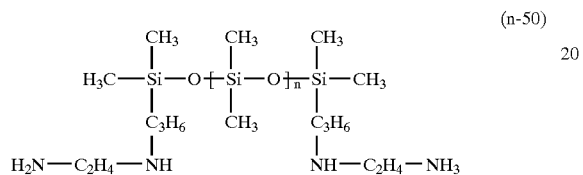

with phenyl isocyanate.

The polymers of formula (VIII) comprising urea or urethane groups in the chain of the silicone polymer may be obtained by reaction between a silicone containing $\alpha,\omega$-$NH_2$ or —OH end groups, of formula:

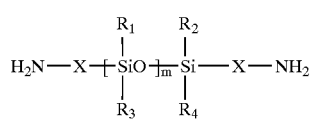

in which m, $R^1$, $R^2$, $R^3$, $R^4$ and X are as defined for formula (I) and a diisocyanate OCN—Y—NCO in which Y has the meaning given in formula (I); and optionally a diol or diamine coupling agent of formula $H_2N$—$B^2$—$NH_2$ or HO—$B^2$—OH, in which $B^2$ is as defined in formula (IX).

According to the stoichiometric proportions between the two reagents, diisocyanate and coupling agent, Y may have the formula (IX) with d equal to 0 or d equal to 1 to 5.

As in the case of the polyamide silicones of formula (II) or (III), it is possible to use in the invention polyurethane or polyurea silicones containing moieties of different length and structure, in particular moieties whose lengths differ by the number of silicone units. In this case, the copolymer may correspond, for example, to the formula:

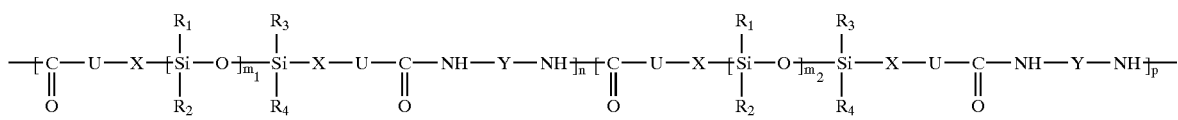

in which $R^1$, $R^2$, $R^3$, $R^4$, X, Y and U are as defined for formula (VIII) and $m_1$, $m_2$, n and p are as defined for formula (V).

Branched polyurethane or polyurea silicones may also be obtained using, instead of the diisocyanate OCN—Y—NCO, a triisocyanate of formula:

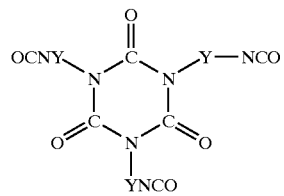

A polyurethane or polyurea silicone containing branches comprising an organosiloxane chain with groups capable of establishing hydrogen interactions is thus obtained. Such a polymer comprises, for example, a moiety corresponding to the formula:

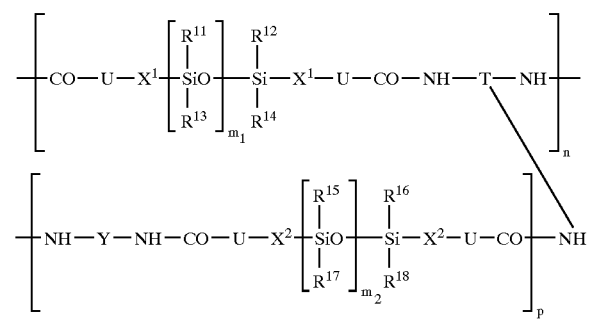

in which $X^1$ and $X^2$, which are identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are numbers in the range from 1 to 1000, and p is an integer ranging from 2 to 500.

As in the case of the polyamides, this copolymer can also comprise polyurethane silicone moieties without branching.

In another embodiment of the invention, the siloxane-based polyureas and polyurethanes that are preferred are:

polymers of formula (VIII) in which m is from 15 to 50;

mixtures of two or more polymers in which at least one polymer has a value of m in the range from 15 to 50 and at least one polymer has a value of m in the range from 30 to 50;

polymers of formula (XII) with $m_1$ chosen in the range from 15 to 50 and $m_2$ chosen in the range from 30 to 500 with the portion corresponding to $m_1$ representing 1% to 99% by weight of the total weight of the polymer and the portion corresponding to $m_2$ representing 1% to 99% by weight of the total weight of the polymer;

mixtures of polymer of formula (VIII) combining
1) 80% to 99% by weight of a polymer in which n is equal to 2 to 10 and in particular 3 to 6, and
2) 1% to 20% of a polymer in which n is in the range from 5 to 500 and in particular from 6 to 100, copolymers comprising two moieties of formula (VIII) in which at least one of the groups Y contains at least one hydroxyl substituent;

polymers of formula (VIII) synthesized with at least one portion of an activated diacid (diacid chloride, dianhydride or diester) instead of the diacid;

polymers of formula (VIII) in which X represents —$(CH_2)_3$— or —$(CH_2)_{10}$—; and polymers of formula (VIII) in which the polymers end with a multifunctional chain chosen from the group consisting of monofunctional amines, monofunctional acids, monofunctional alcohols, including fatty acids, fatty alcohols and fatty amines, such as, for example, octylamine, octanol, stearic acid and stearyl alcohol.

As in the case of the polyamides, copolymers of polyurethane or polyurea silicone and of hydrocarbon-based polyurethane or polyurea may be used in the invention by performing the reaction for synthesizing the polymer in the presence of an α,ω-difunctional block of non-silicone nature, for example a polyester, a polyether or a polyolefin.

As has been seen previously, gelling agents consisting of homopolymers or copolymers of the invention may contain siloxane moieties in the main chain of the polymer and groups capable of establishing hydrogen interactions, either in the main chain of the polymer or at the ends thereof, or on side chains or branches of the main chain. This may correspond to the following five arrangements:

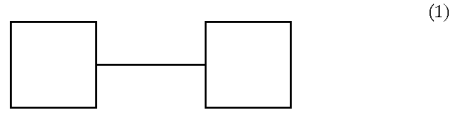
(1)

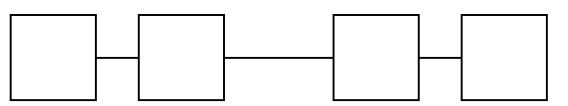
(2)

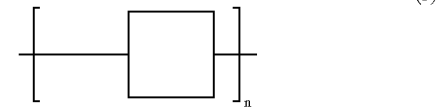
(3)

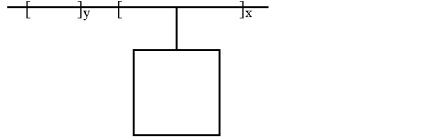
(4)

-continued

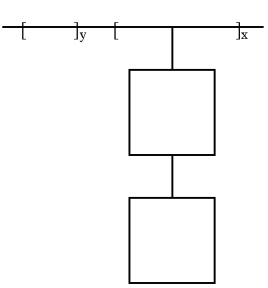
(5)

in which the continuous line is the main chain of the siloxane polymer and the squares represent the groups capable of establishing hydrogen interactions.

In case (1), the groups capable of establishing hydrogen interactions are arranged at the ends of the main chain.

In case (2), two groups capable of establishing hydrogen interactions are arranged at each of the ends of the main chain.

In case (3), the groups capable of establishing hydrogen interactions are arranged within the main chain in repeating moieties.

In cases (4) and (5), these are copolymers in which the groups capable of establishing hydrogen interactions are arranged on branches of the main chain of a first series of moieties that are copolymerized with moieties not comprising groups capable of establishing hydrogen interactions. The values n, x and y are such that the polymer has the desired properties in terms of an agent for gelling fatty phases based on silicone oil.

As examples of polymers that may be used, mention may be made of the silicone polyamides obtained in accordance with Examples 1 and 2 of document U.S. Pat. No. 5,981,680.

The polymers and copolymers used as gelling agents in the composition of the invention advantageously have a softening point from 50 to 130° C. Preferably, they have a softening point ranging from 65 to 150° C. and better still from 70° C. to 130° C. This softening point is lower than that of the known structuring polymers, which facilitates the use of the polymers that are the subject of the invention, and limits the deteriorations of the liquid fatty phase.

As noted above, the siloxane-based polyamides used as thickening agents in base and cosmetic compositions of the present invention contain both siloxane units and amide linkages. The siloxane units provide compatibility with the silicone fluid (for example with the cyclomethicones), while the amide linkages and the spacing and selection of the locations of the amide linkages facilitate gelation and the formation of cosmetic products.

In the base composition, the polyamide gelling agent can be used in an amount of 0.1–80 percent by weight, more particularly 0.5–30 percent by weight and most particularly 1–20 percent by weight. It is preferred that the gellant not exceed 50 percent by weight of the base composition. The silicone fluid portion is in the range of 5–95 percent by weight, more particularly 10–80 percent by weight, even more particularly 20–80 percent by weight. Optionally, additional solvents, mixtures of solvents or cosmetic additives may be added to the base composition. Suitable additional solvents are those which are either themselves or in mixtures with other solvents miscible in the originally selected silicone fluid (for example, C14–C20 fatty alcohols, isopropyl myristate, and PPG-3 myristyl ether).

The siloxane-based polyamide gelling agent can consist of one or more polyamides as described above (or a mixture of these polymers) as the sole gelling agent, or can contain the polyamide admixed with other thickening agents (including conventional gelling agents). The siloxane units provide compatibility with the silicone fluids, while the amide linkages and the spacing and selection of the locations of the amide linkages facilitate gelation and the formation of cosmetic products.

Liquid Fatty Phase

The liquid fatty phase advantageously contains at least 10% and better still at least 30% by weight of silicone oil(s), advantageously having a viscosity of less than 1,000 cSt and better still less than 100 cSt, since the silicone polymers used in the invention are more soluble in silicone oils of low viscosity. It may also contain other non-silicone oils or mixture of oils.

The silicone oils that may be used in the invention may be in particular non-volatile linear polydimethylsiloxanes (PDMSs), that are liquid at room temperature; polydimethylsiloxanes comprising alkyl, alkoxy or phenyl groups, which are pendent and/or at the end of a silicone chain, these groups each containing from 2 to 24 carbon atoms; phenylsilicones, for instance phenyl trimethicones, phenyl dimethicones, phenyl trimethylsiloxydiphenylsiloxanes, diphenyl dimethicones, diphenyl methyldiphenyl trisiloxanes and 2-phenylethyl trimethylsiloxysilicates.

The liquid fatty phase may also contain other non-silicone oils, for example polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearines Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 and better still from 7 to 19 carbon atoms, and $R_6$ represents a branched hydrocarbon-based chain containing from 1 to 40 and better still from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms; $C_8$ to $C_{26}$ fatty alcohols, for instance oleyl alcohol; and mixtures thereof.

The liquid fatty phase may also contain apolar oils such as linear or branched hydrocarbons or fluorocarbons of synthetic or mineral origin, which may be volatile or non-volatile, for instance volatile liquid paraffins (such as isoparaffins or isododecane) or non-volatile liquid paraffins and derivatives thereof, petroleum jelly, polydecenes, hydrogenated polyisobutene such as parleam and squalane, and mixtures thereof.

Generally, the liquid fatty phase represents from 5% to 98.4% of the total weight of the composition and better still from 20% to 75%.

In the emulsion approach the internal phase consists of a liquid solution involving solvents such as water, propylene glycol, dipropylene glycol, tripropylene glycol, ethanol, etc. The base composition of the invention is incorporated into the emulsion that containing water, humectants, surfactants, preservatives, sunscreens, dry particulate matter, and the like. Generally the ranges of these ingredients are 0.1–80% water, 0.01–10% humectants, 0.01–5% surfactants, 0.001–5% preservatives, and 0.001–5% sunscreens.

The compositions of the invention, in one embodiment, may comprise at least one other silicone which acts as an additional film former.

In one embodiment the film former may be a polymethylsilsesquioxane film former such as Belsil PMS MK, also referred to as Resin MK, available from Wacker Chemie. This polymethylsilsesquioxane film former is a polymer comprising polymerized repeating units of $CH_3SiO_{3/2}$ (T units) and may also contain up to 1% by weight or by mole of units of the formula $(CH_3)_2SiO_{2/2}$ (D units). The weight-average molecular weight of this polymer has been estimated to be 10,000. It is believed that the polymers are in a "cage" and "ladder" configuration, as exemplified in the figures below. The majority of the polymer is in the "ladder" configuration, wherein the ends of the polymer are capped with ethoxy ($CH_3CH_2O$) groups. The ethoxy groups are generally present in an amount of 4.5% by weight and the mole percent is generally 7% (silicone units). As ethoxy groups may react with water, a small and variable amount of SiOH may also be present in the polymer.

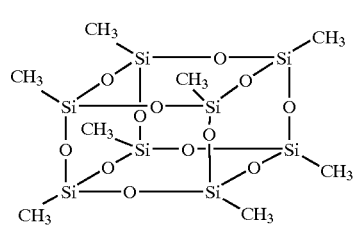

Cage

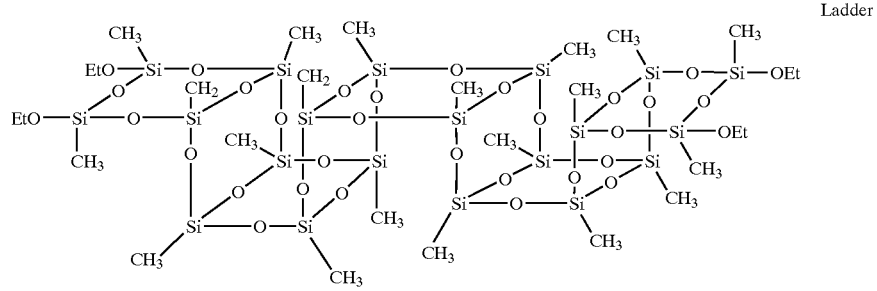

Ladder

Another non-limiting example of the at least one polymethylsilsesquioxane film former suitable for use in the present invention is KR-220L, which is available from SHIN-ETSU. This polymethylsilsesquioxane film former is composed of silicone T-units (i.e., those of formula $CH_3SiO_{3/2}$) and has Si—OH (or silanol) end units. There are no D units in KR-220L.

Other non-limiting examples of the at least one polymethylsilsesquioxane film former that may be useful in the practice of the invention include KR-242A (which is comprised of methyl T units (98%) and dimethyl D units (2%) and has Si—OH end units) and KR-251 (which is comprised of methyl T units (88%) and dimethyl D units (12%) and has Si—OH end units), both of which are available from SHIN-ETSU.

Depending on the application, the concentration of the at least one polymethylsilsesquioxane film former in the presently claimed composition may vary considerably. One of skill in the art will be able to determine routinely the amount of the at least one polymethylsilsesquioxane film former depending on the desired application.

In another embodiment, the silicone film former may be chosen from siloxysilicates. In another embodiment, the siloxysilicate is trimethylsiloxysilicate. Trimethylsiloxysilicate (TMS) is commercially available from General Electric under the tradename SR1000 and from Wacker under the tradename TMS 803. Further, the trimethylsiloxysilicate may be in the form of a powder. TMS is commercially available, for example, from Dow Chemical, in a solvent, such as for example, cyclomethicone. However, according to the present invention, TMS may be used in the form of 100% active material, that is, not in a solvent. In an embodiment, the at least one silicone film former does not comprise at least one solvent. In another embodiment, the at least one silicone film former does not comprise at least one volatile solvent. In another embodiment, the at least one silicone film former is trimethylsiloxysilicate, wherein the at least one silicone film former does not further comprise at least one solvent.

In an embodiment, the silicone film former is present in the composition in an amount ranging from 0.5% to 20% by weight relative to the total weight of the composition. In another embodiment, the silicone film former is present in an amount ranging from 1% to 10% by weight relative to the total weight of the composition. As discussed above, the silicone film former according to the present invention may be commercially available, and may come from suppliers in the form of a dilute solution. The amounts of the silicone film former disclosed herein therefore reflect the weight percent of active material.

Non-limiting examples of the silicone film former include silicone/(meth)acrylate copolymers, such as those as described in U.S. Pat. Nos. 5,061,481, 5,219,560, and 5,262,087, the disclosures of which are hereby incorporated by reference. Further non-limiting examples of the silicone film former are non-polar silicone copolymers comprising repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the product sold under the tradename KP-545, or acrylates/stearyl acrylate/dimethicone acrylates copolymers, such as those commercially available from Shin-Etsu, for example, the product sold under the tradename KP-561, and acrylates/behenyl acrylate/dimethicone acrylates copolymer, such as those commercially available from Shin-Etsu, for example, the product sold under the tradename KP-562.

Another non-limiting example of at least one silicone film former suitable for use in the present invention are silicone esters comprising units of formulae (XIV) and (XV), disclosed in U.S. Pat. Nos. 6,045,782, 5,334,737, and 4,725,658, the disclosures of which are hereby incorporated by reference:

$$R_a R^E_b SiO_{[4-(a+b)/2]} \quad \text{(XIV); and}$$

$$R'_x R^E_y SiO_{1/2} \quad \text{(XV)}$$

wherein
R and R', which may be identical or different, are each chosen from optionally substituted hydrocarbon groups;
a and b, which may be identical or different, are each a number ranging from 0 to 3, with the proviso that the sum of a and b is a number ranging from 1 to 3,
x and y, which may be identical or different, are each a number ranging from 0 to 3, with the proviso that the sum of x and y is a number ranging from 1 to 3;
$R^E$, which may be identical or different, are each chosen from groups comprising at least one carboxylic ester.

In an embodiment, $R^E$ groups are chosen from groups comprising at least one ester group formed from the reaction of at least one acid and at least one alcohol. In an embodiment, the at least one acid comprises at least two carbon atoms. In another embodiment, the at least one alcohol comprises at least ten carbon atoms. Non-limiting examples of the at least one acid include branched acids such as isostearic acid, and linear acids such as behenic acid. Non-limiting examples of the at least one alcohol include monohydric alcohols and polyhydric alcohols, such as n-propanol and branched etheralkanols such as (3,3,3-trimethylolpropoxy)propane.

Further non-limiting examples of the at least one silicone film former include liquid siloxy silicates and silicone esters such as those disclosed in U.S. Pat. No. 5,334,737, such as diisostearoyl trimethylolpropane siloxysilicate and dilauroyl trimethylolpropane siloxy silicate, which are commercially available from General Electric under the tradenames SF 1318 and SF 1312, respectively.

Further non-limiting examples of the at least one copolymer include polymers comprising a backbone chosen from vinyl polymers, methacrylic polymers, and acrylic polymers and at least one chain chosen from pendant siloxane groups and pendant fluorochemical groups. Non-limiting examples of such polymers comprise at least one unit derived from at least one A monomer, at least one unit derived from at least one C monomer, at least one unit derived from D monomers, and, optionally, at least one unit derived from at least one B monomer, wherein:

A, which may be identical or different, are each chosen from free-radically-polymerizable acrylic esters of at least one alcohol chosen from 1,1,-dihydroperfluoroalkanols, omega-hydridofluoroalkanols, fluoroalkylsulfonamido alcohols, cyclic fluoroalkyl alcohols, and fluoroether alcohols, and analogs of any of the foregoing at least one alcohols, and free-radically-polymerizable methacrylic esters of at least one alcohol chosen from 1,1,-dihydroperfluoroalkanols, omega-hydridofluoroalkanols, fluoroalkylsulfonamido alcohols, cyclic fluoroalkyl alcohols, and fluoroether alcohols, and analogs of any of the foregoing at least one alcohols;

B, which may be identical or different, are each chosen from reinforcing monomers which are copolymerizable with at least one A monomer;

C, which may be identical or different, are each chosen from monomers having the formula:

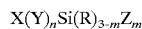

wherein

X is chosen from vinyl groups which are copolymerizable with at least one A monomer and at least one B monomer, Y is chosen from divalent allylene groups, divalent arylene groups, divalent alkarylene groups, and divalent aralkylene groups, wherein the groups comprise from 1 to 30 carbon atoms, and further wherein the groups optionally further comprise at least one group chosen from ester groups, amide groups, urethane groups, and urea groups;

n is zero or 1;

m is a number ranging from 1 to 3;

R, which may be identical or different, are each chosen from hydrogen, $C_1$–$C_4$ alkyl groups, aryl groups, and alkoxy groups; and Z, which may be identical or different, are each chosen from monovalent siloxane polymeric groups; and D, which may be identical or different, are each chosen from free-radically-polymerizable acrylate copolymers and free-radically-polymerizable methacrylate copolymers. Such polymers and their manufacture are disclosed in U.S. Pat. Nos. 5,209,924 and 4,972,037, and WO 01/32737, the disclosures of which are hereby incorporated by reference.

Other non-limiting examples of the at least one copolymer is silicone/acrylate graft terpolymers, for example, those having the formula:

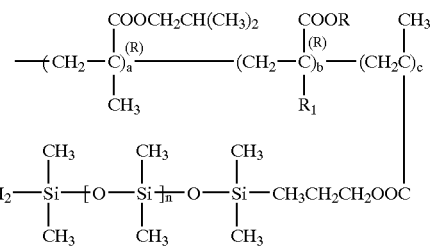

wherein a, b, and c are present in a weight ratio of 69.9:0.1:30 respectively,

R and $R_1$, which may be identical or different, are each chosen from hydrogen and $C_1$–$C_6$ alkyl groups; and m is a number ranging from 100–150.

In an embodiment, m is chosen to provide a macromer having a molecular weight ranging from 8,000 to 12,000, such as 10,000. In another embodiment, m is a number ranging from 124–135, such as 130. Non-limiting examples of these copolymers are described in WO 01/32727 A1, the disclosure of which is hereby incorporated by reference.

In another embodiment of the invention, the at least one copolymer comprises a backbone chosen from vinyl backbones, methacrylic backbones, and acrylic polymeric backbones and further comprises at least one pendant siloxane group. Non-limiting examples of such polymers are disclosed in U.S. Pat. Nos. 4,693,935, 4,981,903, 4,981,902, the disclosures of which are hereby incorporated by reference.

In an embodiment, the at least one copolymer comprises at least one A monomer, at least one C monomer, and, optionally at least one B monomer, wherein the at least one A monomer is chosen from free-radically-polymerizable vinyl monomers, free-radically-polymerizable methacrylate monomers, and free-radically-polymerizable acrylate monomers; the at least one B monomer, if present, is chosen from at least one reinforcing monomer copolymerizable with the at least one A monomer, and the at least one C monomer is chosen from monomers having the formula:

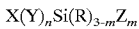

wherein:

X is chosen from vinyl groups which are copolymerizable with the at least one A monomer and with the at least one B monomer;

Y is chosen from divalent groups;

n is zero or 1;

m is a number ranging from 1 to 3;

R, which may be identical or different, are each chosen from hydrogen, optionally substituted $C_1$–$C_{10}$ alkyl groups, optionally substituted phenyl groups, and optionally substituted $C_1$–$C_{10}$ alkoxy groups; and Z, which may be identical or different, are each chosen from monovalent siloxane polymeric groups.

Non-limiting examples of A monomers include methacrylic acid esters of $C_1$–$C_{12}$ linear alcohols, methacrylic acid esters of $C_1$–$C_{12}$ of branched alcohols, styrene monomers, vinyl esters, vinyl chloride monomers, vinylidene chloride monomers, and acryloyl monomers.

Non-limiting examples of B monomers include acrylic monomers comprising at least one group chosen from hydroxyl, amino, and ionic groups, and methacrylic monomers comprising at least one group chosen from hydroxyl, amino, and ionic groups. Non-limiting examples of ionic groups include quaternary ammonium groups, carboxylate salts, and sulfonic acid salts.

The C monomers are the same as those described for the C monomers in the previous paragraphs.

In another embodiment of the invention, the at least one copolymer is chosen from vinyl-silicone graft copolymers having the following formula and vinyl-silicone block copolymers having the following formula:

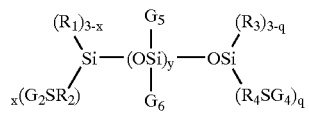

wherein
- $G_5$, which may be identical or different, are each chosen from alkyl groups, aryl groups, aralkyl groups, alkoxy groups, alkylamino groups, fluoroalkyl groups, hydrogen, and -ZSA groups, wherein
  A is chosen from vinyl polymeric segments comprising at least one polymerized free-radically-polymerizable monomer, and
  Z is chosen from divalent $C_1$-$C_{10}$ alkylene groups, divalent aralkylene groups, divalent arylene groups, and divalent alkoxylalkylene groups. In an embodiment Z is chosen from methylene groups and propylene groups.
- $G_6$, which may be identical or different, are each chosen from alkyl groups, aryl groups, aralkyl groups, alkoxy groups, alkylamino groups, fluoroalkyl groups, hydrogen, and -ZSA groups, as defined above;
- $G_2$ comprises A;
- $G_4$ comprises A;
- $R_1$, which may be identical or different, are each chosen from alkyl groups, aryl groups, aralkyl groups, alkoxy groups, alkylamino groups, fluoroalkyl groups, hydrogen, and hydroxyl. In one embodiment, $R_1$ is chosen from $C_1$–$C_4$ alkyl groups, such as methyl groups, and hydroxyl.
- $R_2$, which may be identical or different, are each chosen from divalent $C_{1-10}$ alkylene groups, divalent arylene groups, divalent aralkylene groups, and divalent alkoxyalkylene groups. In one embodiment, $R_2$ is chosen from divalent $C_1$–$C_3$ alkylene groups and divalent $C_7$–$C_{10}$ aralkylene groups. In another embodiment, $R_2$ is chosen from —$CH_2$— groups and divalent 1,3-propylene groups.
- $R_3$, which may be identical or different, are each chosen from alkyl groups, aryl groups, aralkyl groups alkoxy groups, alkylamino groups, fluoroalkyl groups, hydrogen, and hydroxyl. In one embodiment, $R_3$ is chosen from $C_1$–$C_4$ alkyl groups and hydroxyl. In another embodiment, $R_3$ is chosen from methyl groups.
- $R_4$, which may be identical or different, are each chosen from divalent $C_1$–$C_{10}$ alkylene groups, divalent arylene groups, divalent aralkylene groups, and divalent alkoxyalkylene groups. In one embodiment, $R_4$ is chosen from divalent $C_1$–$C_3$ alkylene groups and divalent $C_7$–$C_{10}$ aralkylene groups. In another embodiment, $R_4$ is chosen from divalent —$CH_2$— groups and divalent 1,3-propylene groups.
- x is a number ranging from 0 to 3;
- y is a number greater than or equal to 5. In an embodiment, y ranges from 10 to 270, and in another embodiment, y ranges from 40 to 270.
- q is a number ranging from 0 to 3;

Non-limiting examples of these polymers are described in U.S. Pat. No. 5,468,477, the disclosure of which is hereby incorporated by reference. A non-limiting example of such polymers is poly(dimethylsiloxane)-g-poly(isobutyl methacrylate), which is commercially available from 3M Company under the tradename VS 70 IBM.

In an embodiment, the at least one copolymer is present in the composition in an amount ranging from 0.2% to 30% by weight relative to the total weight of the composition. In another embodiment, the at least one copolymer is present in an amount ranging from 1% to 10% by weight relative to the total weight of the composition. One of ordinary skill in the art will recognize that the at least one copolymer according to the present invention may be commercially available, and may come from suppliers in the form of a dilute solution. The amounts of the at least one copolymer disclosed herein therefore reflect the weight percent of active material.

Further, the composition of the present invention may also comprise at least one coloring agent. The at least one coloring agent may be chosen from pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the pigments may be present in the composition in a concentration ranging up to 50% by weight of the total weight of the composition, such as from 0.5% to 40%, and further such as from 2% to 30%. In the case of certain products, the pigments, including nacreous pigments, may, for example, represent up to 50% by weight of the composition.

Further, the composition of the present invention may contain waxes. For the purposes of the invention, the waxes are those generally used in cosmetics and dermatology; they are, for example, of natural origin, for instance beeswax, carnauba wax, candelilla wax, ouricury wax, Japan wax, cork fibre wax, sugar cane wax, paraffin wax, lignite wax, microcrystalline waxes, lanolin wax, montan wax, ozokerites and hydrogenated oils such as hydrogenated jojoba oil as well as waxes of synthetic origin, for instance polyethylene waxes derived from the polymerization of ethylene, waxes obtained by Fischer-Tropsch synthesis, fatty acid esters and glycerides that are solid at 40° C., for example, at above 55° C., silicone waxes such as alkyl- and alkoxy-poly (di)methylsiloxanes and/or poly(di)methyl-siloxane esters that are solid at 40° C., for example, at above 55° C.

Emollients and/or humectants that may be used in the compositions of the invention include glycerin, propylene glycol, cyclomethicone, dimethicone, and emollients and other similar ingredients disclosed in the *International Cosmetic Ingredient Dictionary and Handbook Vol. 4* (9$^{th}$ ed. 2002), more particularly the emollients disclosed on pages 2930–2936. The disclosure of the *International Cosmetic Ingredient Dictionary and Handbook Vol. 4*, pages 2930–2936, is hereby incorporated by reference.

The compositions of the invention may further include formulation aids which are usually employed in the field of application envisaged. The formulation aids used in the present invention can be, but are not limited to, fatty substances. Useful fatty substances include, but are not limited to, organic and organosilicone emulsifiers for water-in-oil systems. Examples of organic emulsifiers include any ethoxylated surfactants known in the art such as Polysorbate-20, Laureth-7, Laureth-4, Sepigel® 305 available from SEPPIC and other similar ingredients disclosed in the *International Cosmetic Ingredient Dictionary and Handbook Vol. 4* (9$^{th}$ ed. 2002), more particularly the emulsifiers disclosed on pages 2962–2971. The disclosure of the *International Cosmetic Ingredient Dictionary and Handbook Vol. 4*, pages 2962–2971, is hereby incorporated by reference. Examples of organosilicone emulsifiers include cetyl dimethicone copolyol-polyglyceryl-4-isostearate-hexylaurate (ABIL® WE 09) available from Goldschmidt Chemical Corporation, Cetyl Dimethicone Copolyol (ABIL® EM 90), (ABIL® EM 97), Laurylmethicone Copolyol (5200), Cyclomethicone (and) Dimethicone Copolyol (DC 5225 C and DC 3225 C) available from GE Silicones, Cyclopentasiloxane & Dimethicone Copolyol (GE SF 1528) or any other formulation aids known by one of skill in the art. Other fatty substances useful as formulation aids include but are not limited to, silicones in esterified or unesterified liquid form or in esterified solid form, such as behenate dimethicone; and non-silicone fatty substances including oils such as vegetable and mineral oil; animal and/or synthetic waxes such as beeswax, parafin, rice bran wax, candelilla wax, carnauba wax and derivatives thereof; and hydrocarbon gels or bentone type gels, such as Gel SS71, Gel EA2786, Quaternium-18 Bentonite, 38 CE, Gel ISD V or Gel ISD.

These substances may be selected variously by the person skilled in the art in order to prepare a composition which has the desired properties, for example, consistency or texture.

Plasticizers may also be added to the compositions to improve the flexibility and cosmetic properties of the resulting formulation. Plasticizers are materials which soften synthetic polymers. They are frequently required to avoid brittleness and cracking of film formers. One skilled in the art may routinely vary the amount of plasticizer desired based on the properties desired and the application envisaged. Plasticizers useful in the practice of the invention include lecithin, polysorbates, dimethicone copolyol, glycols, citrate esters, glycerin, dimethicone, and other similar ingredients disclosed in the *International Cosmetic Ingredient Dictionary and Handbook Vol. 4* (9$^{th}$ ed. 2002), more particularly the plasticizers disclosed on page 2927. The disclosure of the *International Cosmetic Ingredient Dictionary and Handbook Vol. 4*, page 2927, is hereby incorporated by reference.

In one embodiment, the composition may contain sunscreens. Sunscreens may be inorganic nanoparticles or organic compounds. In one embodiment the nanoparticles are inorganic compounds composed essentially of metal oxides. Suitable metal oxides comprise one or more of iron oxide, aluminum oxide, zirconium oxide, vanadium oxide, niobium oxide, tantalum oxide, chromium oxide, molybdenum oxide, tungsten oxide, cobalt oxide, nickel oxide, cerium cupric oxide, zinc oxide, tin oxide, antimony oxide titanium dioxide and mixtures thereof, among others. In yet another embodiment titanium dioxide and zinc oxide are used. Without being limited to theory, in most cases the metal oxide nanoparticles provide a sun protection benefit by diffracting the ultraviolet light. The elemental size of 1 nanoparticle is typically from less than 1 m in size, including from about 100 nm to about 500 nm, including about 200 nm to about 350 nm.

Sunscreens according to this invention which are chemical absorbers actually absorb harmful ultraviolet radiation. It is well known that chemical absorbers are classified, depending on the type of radiation they protect against, as either UV-A or UV-B absorbers. UV-A absorbers generally absorb radiation in the 320 to 400 nm region of the ultraviolet spectrum. UV-A absorbers include anthranilates, benzophenones, and dibenzoyl methanes. UV-B absorbers generally absorb radiation in the 280 to 320 nm region of the ultraviolet spectrum. UV-B absorbers include p-aminobenzoic acid derivatives, camphor derivatives, cinnamates, and salicylates.

Classifying the chemical absorbers generally as UV-A or UV-B absorbers is accepted within the industry. However, a more precise classification is one based upon the chemical properties of the sunscreens. There are eight major classifications of sunscreen chemical properties which are discussed at length in "Sunscreens—Development, Evaluation and Regulatory Aspects," by N. Shaath et al., 2nd. Edition, pages 269–273, Marcel Dekker, Inc. (1997). This discussion, in its entirety, is incorporated by reference herein.

The sunscreens which may be formulated according to the present invention typically comprise chemical absorbers, but may also comprise physical blockers. Exemplary sunscreens which may be formulated into the compositions of the present invention are chemical absorbers such as p-aminobenzoic acid derivatives, anthranilates, benzophenones, camphor derivatives, cinnamic derivatives, dibenzoyl methanes, diphenylacrylate derivatives, salicylic derivatives, triazine derivatives, benzimidazole compounds, bis-benzoazolyl derivatives, methylene bis-(hydroxyphenylbenzotriazole) compounds, the sunscreen polymers and silicones, or mixtures thereof. These are variously described in U.S. Pat. Nos. 2,463,264, 4,367,390, 5,166,355 and 5,237,071 and in EP-0,863,145, EP-0,517, 104, EP-0,570,838, EP-0,796,851, EP-0,775,698, EP-0,878, 469, EP-0,933,376, EP-0,893,119, EP-0,669,323, GB-2,303, 549, DE-1,972,184 and WO-93/04665, also expressly incorporated by reference. Also exemplary of the sunscreens which may be formulated into the compositions of this invention are physical blockers such as cerium oxides, chromium oxides, cobalt oxides, iron oxides, red petrolatum, silicone-treated titanium dioxide, titanium dioxide, zinc oxide, and/or zirconium oxide, or mixtures thereof.

A wide variety of sunscreens is described in U.S. Pat. No. 5,087,445, issued to Haffey et al. on Feb. 11, 1992; U.S. Pat.

No. 5,073,372, issued to Turner et al. on Dec. 17, 1991; and Chapter VIII of *Cosmetics and Science and Technology* by Segarin et al., pages 189 et seq. (1957), all of which are incorporated herein by reference in their entirety.

Sunscreens which may be formulated into the compositions of the instant invention are those selected from among: aminobenzoic acid, amyldimethyl PABA, cinoxate, diethanolamine p-methoxycinnamate, digalloyl trioleate, dioxybenzone, 2-ethoxyethyl p-methoxycinnamate, ethyl 4-bis(hydroxypropyl)aminobenzoate, 2-ethylhexyl-2-cyano-3,3-diphenylacrylate, ethylhexyl p-methoxycinnamate, 2-ethylhexyl salicylate, glyceryl aminobenzoate, homomenthyl salicylate, homosalate, 3-imidazol-4-ylacrylic acid and ethyl ester, methyl anthranilate, octyldimethyl PABA, 2-phenylbenzimidazole-5-sulfonic acid and salts, red petrolatum, sulisobenzone, titanium dioxide, triethanolamine salicylate, N,N,N-trimethyl-4-(2-oxoborn-3-ylidene methyl)anillinium methyl sulfate, and mixtures thereof.

Sunscreens active in the UV-A and/or UV-B range can also include:
p-aminobenzoic acid,
oxyethylene (25 mol) p-aminobenzoate,
2-ethylhexyl p-dimethylaminobenzoate,
ethyl N-oxypropylene p-aminobenzoate,
glycerol p-aminobenzoate,
4-isopropylbenzyl salicylate,
2-ethylhexyl 4-methoxycinnamate,
methyl diisopropylcinnamate,
isoamyl 4-methoxycinnamate,
diethanolamine 4-methoxycinnamate,
3-(4'-trimethylammunium)-benzyliden-bornan-2-one methylsulfate,
2-hydroxy-4-methoxybenzophenone,
2-hydroxy-4-methoxybenzophenone-5-sulfonate,
2,4-dihydroxybenzophenone,
2,2',4,4'-tetrahydroxybenzophenone,
2,2'-dihydroxy-4,4'dimethoxybenzophenone,
2-hydroxy-4-n-octoxybenzophenone,
2-hydroxy-4-methoxy-4'-methoxybenzophenone,
-(2-oxoborn-3-ylidene)-tolyl-4-sulfonic acid and soluble salts thereof,
3-(4'-sulfo)benzyliden-bornan-2-one and soluble salts thereof,
3-(4'methylbenzylidene)-d,l-camphor,
3-benzylidene-d,l-camphor,
benzene 1,4-di(3-methylidene-10-camphosulfonic) acid and salts thereof (the product Mexoryl SX described in U.S. Pat. No. 4,585,597 issued to Lange et al. on Apr. 29, 1986),
urocanic acid,
2,4,6-tris[p-(2'-ethylhexyl-1'-oxycarbonyl)-anilino]-1,3,5-triazine,
2-[(p-(tertiobutylamido)anilino]-4,6-bis-[(p-(2'-ethylhexyl-1'-oxycarbonyl)anilino]-1,3,5-triazine,
2,4-bis{[4-(2-ethyl-hexyloxy)]-2-hydroxy]-phenyl}-6-(4-methoxy-phenyl)-1,3,5-triazine ("TINOSORB S" marketed by Ciba),
the polymer of N-(2 et 4)-[(2-oxoborn-3-yliden)methyl]benzyl]-acrylamide,
1,4-bisbenzimidazolyl-phenylen-3,3',5,5'-tetrasulfonic acid and salts thereof,
the benzalmalonate-substituted polyorganosiloxanes,
the benzotriazole-substituted polyorganosiloxanes (Drometrizole Trisiloxane),
dispersed 2,2'-methylene-bis-[6-(2H-benzotriazol-2-yl)-4-(1,1,3,3-tetramethylbutyl)phenol] such as that marketed under the trademark MIXXIM BB/100 by Fairmount Chemical, or micronized in dispersed form thereof such as that marketed under the trademark TINOSORB M by Ciba-Geigy, and
solubilized 2,2'-methylene-bis-[6-(2H-benzotriazol-2-yl)-4-(methyl)phenol] such as that marketed under the trademark MIXXIM BB/200 by Fairmount Chemical.

Typically combinations of one of more of these sunscreens are used.

The dibenzoyl methane derivatives other than avobenzone are described, for example, in FR-2,326,405, FR-2,440,933 and EP-0,114,607, hereby expressly incorporated by reference.

Other dibenzoyl methane sunscreens other than avobenzone include (whether singly or in any combination):
2-methyldibenzoylmethane
4-methyldibenzoylmethane
4-isopropyldibenzoylmethane
4-tert.-butyldibenzoylmethane
2,4-dimethyldibenzoylmethane
2,5-dimethyldibenzoylmethane
4,4'-diisopropyldibenzoylmethane
4,4'-dimethoxydibenzoylmethane
2-methyl-5-isopropyl-4'-methoxydibenzoylmethane
2-methyl-5-tert.-butyl-4'-methoxydibenzoylmethane
2,4-dimethyl-4'-methoxydibenzoylmethane
2,6-dimethyl-4-tert.-butyl-4'-methoxydibenzoylmethane Additional sunscreens that can be used are described in pages 2954–2955 of the *International Cosmetic Ingredient Dictionary and Handbook* ($9^{th}$ ed. 2002).

According to the present invention, the compositions may further comprise at least one filler. As used herein, the term "filler" means any particle that is solid at room temperature and atmospheric pressure, used alone or in combination, which does not react chemically with the various ingredients of the emulsion and which is insoluble in these ingredients, even when these ingredients are raised to a temperature above room temperature and in particular to their softening point or their melting point. In an embodiment, the at least one filler has a melting point at least greater than 1700° C., for example, greater than 2000° C. In an embodiment, the at least one filler may have an apparent diameter ranging from 0.01 $\mu$m to 150 $\mu$m, such as from 0.5 $\mu$m to 120 $\mu$m, for example from 1 $\mu$m to 80 $\mu$m. An apparent diameter corresponds to the diameter of the circle into which the elementary particle fits along its shortest dimension (thickness for leaflets). Further, the at least one filler may be absorbent, i.e., capable in particular of absorbing the oils of the composition and also the biological substances secreted by the skin, may be surface-treated, e.g., to make it lipophilic, and/or may be porous so as to absorb the sweat and/or sebum secreted by the skin.

The at least one filler may be chosen from inorganic and organic fillers, and may have any shape such as lamellar, spherical and/or oblong. Non-limiting examples of the at least one inert filler include talc, mica, silica, kaolin, polyamide powders (such as Nylon® powder, and such as the product sold by Atochem as Orgasol®), poly-β-alanine powders, polyethylene powders, acrylic polymer powders (such as polymethyl methacrylate (PMMA) powder, for instance the product sold by Wacker as Covabead LH-85 (particle size 10–12 $\mu$m) and the acrylic acid copolymer powder sold by Dow Corning as Polytrap®), polytetrafluoroethylene (Teflon®) powders, lauroyllysine, boron nitride, silica, kaolin, starch, starch derivatives, hollow polymer microspheres (such as those hollow polymer microspheres formed from polyvinylidene chloride and acrylonitrile, for instance the product sold by Nobel Industrie as Expancel®), and polymerized silicone microspheres (such as those polymerized silicone microspheres sold by Toshiba as Tospearl®), precipitated calcium carbonate, magnesium carbonate and hydrocarbonate, hydroxyapatite, hollow silica microspheres (such as the product sold by Maprecos as Silica Beads®), glass microcapsules, ceramic microcapsules, and polyester particles.

Other embodiments of the inventions may include other cosmetically or dermatologically acceptable additional ingredients such as thickeners, preservatives or biological actives and any other ingredient that a person of ordinary skill in the art may identify. These additional ingredients may be found in the *International Cosmetic Ingredient Dictionary and Handbook* (9$^{th}$ ed. 2002).

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

The invention is illustrated in more detail in the following examples.

EXAMPLE 1

Foundation

| Phase | Ingredient Name | % w/w |
|---|---|---|
| A | Cyclopentasiloxane and Dimethicone Copolyol[1] | 8.00 |
|  | Polyglyceryl-4-isostearate and Hexyl Laurate and Cetyl PEG/PPG-10/1 Dimethicone[2] | 3.50 |
|  | Treated Pigments | 9.90 |
| B1 | Volatile Oil | 16.10 |
|  | Siloxane based polyamide[3] | 1.00 |
|  | Silicone Acrylates[4] | 12.00 |
| B2 | Fillers | 6.00 |
| B3 | Preservative | 0.40 |
|  | Disteardimonium Hectorite | 0.60 |
|  | Propylene Carbonate | 0.20 |
| C | Water | 40.00 |
|  | Magnesium Sulfate | 1.00 |
|  | Preservatives | 0.70 |
|  | Non-ionic emulsifier | 0.50 |
|  |  | 100.00 |

[1]Dow Corning DC5225C
[2]ABIL WE 09
[3]Dow Corning DC2-8179 (DP = 100)
[4]KP545

Phase A ingredients were mixed well and ground with a Silverson homogenizer at a speed of 6000 rpm. Separately the phase B1 ingredients were heated to 80 to 85° C. with stirring for 10–15 minutes or until dissolution of the siloxane based polyamide. Phase A and B1 were then combined in the main beaker and mixed well at 70 to 75° C. Phase B2 was added to the main beaker and was mixed well or until uniform. In a separate side beaker, phase C was heated to 70 to 75° C. Emulsification was carried out by adding phase C to main beaker with the use of a homogenizer at medium/high speed. The batch was cooled to room temperature with a paddle stirring.

This composition exhibited good wear, excellent transfer-resistance after drying, good water resistance and felt cushiony.

EXAMPLE 2

Foundation

| Phase | Ingredient Name | % w/w |
|---|---|---|
| A | Cyclopentasiloxane and Dimethicone Copolyol[1] | 8.00 |
|  | Polyglyceryl-4-isostearate and Hexyl Laurate and Cetyl PEG/PPG-10/1 Dimethicone[2] | 3.50 |
|  | Pigments | 9.90 |
| B1 | Volatile Oil | 26.10 |
|  | Siloxane based polyamide[3] | 3.00 |
| B2 | Fillers | 6.00 |
| B3 | Preservative | 0.40 |
|  | Disteardimonium Hectorite | 0.60 |
|  | Propylene Carbonate | 0.20 |
| C | Water | 40.00 |
|  | Magnesium Sulfate | 1.00 |
|  | Preservatives | 0.70 |
|  | Non ionic emulsifier | 0.50 |
|  |  | 100.00 |

[1]Dow Corning DC5225C
[2]ABIL WE 09
[3]Dow Corning DC2-8179 (DP = 100)

Phase A ingredients were mixed well and ground with a Silverson homogenizer at a speed of 6000 rpm. Separately the phase B1 ingredients were heated to 80 to 85° C. with stirring for 10–15 minutes or until dissolution of the siloxane based polyamide. Phase A and B1 were then combined in the main beaker and mixed well at 70 to 75° C. Phase B2 was added to the main beaker and was mixed well or until uniform. Disteardimonium Hectorite was added to the main beaker and dispersed well before adding the rest of phase B3 ingredients. In a separate side beaker, phase C was heated to 70 to 75° C. Emulsification was carried out by adding phase C to the main beaker with the use of a homogenizer at medium/high speed. The batch was cooled to room temperature with a paddle stirring.

This composition exhibited good transfer-resistance after drying, good water resistance and felt cushiony.

EXAMPLE 3

Foundation

| Phase | Ingredient Name | % w/w |
|---|---|---|
| A | Cyclopentasiloxane and Dimethicone Copolyol[1] | 8.00 |
|  | Polyglyceryl-4-isostearate and Hexyl Laurate and Cetyl PEG/PPG-10/1 Dimethicone[2] | 3.50 |
|  | Treated Pigments | 9.90 |
| B1 | Volatile Oil | 26.10 |
|  | Siloxane based polyamide[3] | 2.00 |
|  | TiO$_2$/Silicone-Acrylates[4] | 12.00 |
| B2 | Fillers | 6.00 |
| B3 | Preservative | 0.40 |
|  | Disteardimonium Hectorite | 1.00 |
|  | Propylene Carbonate | 0.30 |
| C | Water | 40.00 |
|  | Magnesium Sulfate | 1.00 |
|  | Preservatives | 0.70 |
|  | Laureth-4 | 0.50 |
|  |  | 100.00 |

[1]Dow Corning DC5225C
[2]ABIL WE 09
[3]Dow Corning DC2-8179 (DP = 100)
[4]SPD-T1S: Silicone acrylate treated TiO$_2$ Phase A ingredients were mixed well and ground with a Silverson homogenizer at a speed of 6000 rpm. Separately the phase B1 ingredients were heated to 80 to 85° C. with stirring for 10–15 minutes or until dissolution of the siloxane based polyamide. Phase A and B1 were then combined in the main beaker and mixed well at 70 to 75° C. Phase B2 was added to the main beaker and was mixed well or until uniform. Disteardimonium Hectorite was added to the main beaker and dispersed well before adding the rest of phase B3 ingredients. In a separate side beaker, phase C was heated to 70 to 75° C. Emulsification was carried out by adding phase C to the main beaker with the use of a homogenizer at medium/high speed. The batch was cooled to room temperature with a paddle stirring.

This composition exhibited good transfer-resistance after drying, good water resistance and felt cushiony.

EXAMPLE 4

Foundation

| Phase | Ingredient Name | % w/w |
|---|---|---|
| A | Oil Soluble Sunscreen | 4.00 |
|   | Cyclopentasiloxane and Dimethicone Copolyol[1] | 8.00 |
|   | Treated Pigments | 9.90 |
| B | Volatile Oil | 26.10 |
|   | Siloxane based polyamide[2] | 3.00 |
|   | Polyglyceryl-4-isostearate and Hexyl Laurate and Cetyl PEG/PPG-10/1 Dimethicone[3] | 3.50 |
|   | Preservative | 0.20 |
| C | Fillers | 6.04 |
| D | Water | 42.16 |
|   | Magnesium Sulfate | 1.00 |
|   | Preservatives | 0.30 |
|   | Laureth-4 | 0.50 |
| E | Water | 1.00 |
|   | Preservative | 0.30 |
|   |   | 100.00 |

[1]Dow Corning DC5225C
[2]Dow Corning DC2-8179 (DP = 100)
[3]ABIL WE 09g

Phase A ingredients were mixed well and ground with a Silverson homogenizer at a speed of 6000 rpm. Separately the phase B ingredients were heated to 80 to 85° C. with stirring for 10–15 minutes or until dissolution of siloxane polyamide. Phase A and B were then combined in the main beaker and mixed well at 60 to 65° C. Phase C ingredients (powders) were added to the main beaker and were mixed until uniform. Phase D was heated to 65 to 70° C. in a separate side beaker. Emulsification was carried out by adding phase D to main beaker with the use of a homogenizer at medium/high speed. Cool the batch to 40 to 45° C., then add phase E slowly with good mixing. The batch was then cooled to room temperature with a paddle stirring.

This composition had good wear, exhibited transfer resistance and water resistance while feeling cushiony

EXAMPLE 5

Foundation

| Phase | Ingredient Name | % w/w |
|---|---|---|
| A | Oil Soluble Sunscreen | 4.00 |
|   | Cyclopentasiloxane and Dimethicone Copolyol[1] | 8.00 |
|   | Cyclopentasiloxane and Diphenyl Dimethicone[2] | 8.00 |
|   | Treated Pigments | 10.00 |

-continued

| Phase | Ingredient Name | % w/w |
|---|---|---|
| B1 | Volatile Oil | 18.00 |
|   | Siloxane based polyamide[3] | 3.00 |
|   | Polyglyceryl-4-isostearate and Hexyl Laurate and Cetyl PEG/PPG-10/1 Dimethicone[4] | 3.50 |
|   | Preservative | 0.20 |
|   | Fillers | 6.04 |
| D | Water | 42.16 |
|   | Emollient | 10.00 |
|   | Magnesium Sulfate | 1.00 |
|   | Preservatives | 0.30 |
|   | Laureth-4 | 0.50 |
| E | Water | 1.00 |
|   | Preservative | 0.30 |
|   |   | 100.00 |

[1]Dow Corning DC5225C
[2]Mirasil C-DPDM
[3]Dow Corning DC 2-8179 (DP = 100)
[4]ABIL WE 09

Phase A ingredients were mixed well and ground with a Silverson homogenizer at a speed of 6000 rpm. Separately the phase B ingredients were heated to 80 to 85° C. with stirring for 10–15 minutes or until dissolution of siloxane polyamide. Phase A and B were then combined in the main beaker and mixed well at 60 to 65° C. Phase C ingredients (powders) were added to the main beaker and were mixed until uniform. Phase D was heated to 65 to 70° C. in a separate side beaker. Emulsification was carried out by adding phase D to main beaker with the use of a homogenizer at medium/high speed. Cool the batch to 40 to 45° C., then add phase E slowly with good mixing. The batch was then cooled to room temperature with a paddle stirring.

This composition exhibited good wear, transfer resistance and water resistance

EXAMPLE 6

Lipstick

| Ingredient Name | Trade name | % w/w |
|---|---|---|
| Dimethicone 20 cst | DC200 20 cs (Dow Corning) | 39.04 |
| Polyglyceryl-2-diisostearate | Dermol DGDIS | 40.00 |
| Pigments |   | 0.96 |
| Polyamidodimethylsiloxane[1] | DC2-8179 | 15.0 |
| Diisostearyl malate | Schercemol DSIM | Qsp 100 |

[1]Dow Corning DC 2-9179 (DP = 115)

The ingredients are added together in a beaker, heated to about 80–85° C. while mixing. Once homogeneous, the mixture is milled at 60 to 65° C. until well dispersed. Once dispersed, the mixture was discharged from the mill, transferred to a mixing kettle and heated to 90–95° C. The mill was rinsed with diisostearyl malate for 10–15 minutes and the contents transferred to the mixing kettle. The mixture was mixed until uniform and then poured into molds.

This composition was supple and elastic.

EXAMPLE 7

Lipstick

| Phase | Ingredient Name | Trade name | % w/w |
|---|---|---|---|
| A | Dimethicone 20 cst | DC200 20 cs (Dow Corning) | 20.0 |
| A | Polyglyceryl-2-diisostearate | Dermol DGDIS | 20.5 |
| A | Diisostearyl malate | Schercemol DSIM | 6.0 |
| A | Phenyltrimethicone | Belsil PDM 1000 | 20.0 |
| A | Phenyltrimethicone | DC 556 | 10.0 |
| B | Polyamidodimethylsiloxane[1] | DC2-8179 | 20.0 |
| C | Pigments | | 1.5 |
| C | Fillers | | 2.0 |

[1]Dow Corning DC 2-9179 (DP = 15)

Phase A ingredients were added one by one in a mixing kettle heated to 90–95° C. and mixed until homogeneous. Phase B was added and mixed until homogeneous at 90–95° C. Phase C was added and mixed well. The resulting mixture is poured into molds and allowed to cool to form sticks. This composition was supple and elastic.

EXAMPLE 8

Lip Gloss

| Ingredient | Trade Name | % w/w |
|---|---|---|
| Film Former | SA-70 from 3M | 20.0 |
| Polyamidodimethylsiloxane[1] | DC2-8179 | 8.0 |
| Phenyltrimethicone | DC 556 | 65.1 |
| Pigments | | 6.9 |

[1]Dow Corning DC 2-9179 (DP = 15)

This composition was supple and elastic.
The film forming polymer is introduced under agitation with a magnetic stirrer after the rest of the formula has been heated. The gloss is introduced into a container and applied using a sponge type applicator.

The composition exhibits better wear when compared with one not containing a film forming polymer.

What is claimed is:

1. A transfer-resistant cosmetic composition comprising a siloxane based polyamide is a polymer comprising multiples of a unit represented by the following formula (A):

Formula A

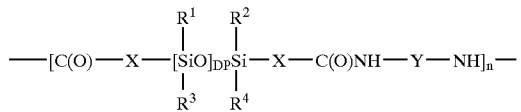

where:
 (a) DP is between 1 and 700;
 (b) n is a number selected from the group consisting of 1–500;
 (c) X is a linear or branched chain alkylene having 1–30 carbons;
 (d) Y is selected from the group consisting of linear or branched chain alkylenes having 1–40 carbons;
 (d) $R^1$, $R^2$, $R^3$ and $R^4$ are the same or different and may be selected from the group consisting of methyl, ethyl, propyl, isopropyl, a siloxane chain, and phenyl a volatile silicone oil is selected from the group consisting of octyltrimethicone, hexyltrimethicone, decamethylcyclcopentasiloxane D5, octamethyl cyclotetrasiloxane D4, dodecamethyl cyclohexasiloxane D6, heptamethyl octyltrisiloxane, decamethyl tetrasiloxane, dodecamethyl pentasiloxane, polydimethylsiloxane at 1.5 centistokes (cSt), polydimethylsiloxane at 2 centistokes, polydimethylsiloxane at 3 centistokes, polydimethylsiloxane at 5 centistokes and their mixtures; and at least one non-silicone volatile oil, wherein said composition is not a deodorant or antiperspirant stick.

2. The transfer-resistant cosmetic composition according to claim 1 wherein the phenyl group may optionally be substituted by 1–3 members from the group consisting of methyl and ethyl.

3. The transfer-resistant cosmetic composition according to claim 1, wherein the degree of polymerization DP is between 15 and 500.

4. The transfer-resistant cosmetic composition according to claim 1, wherein the degree of polymerization DP is between 50 and 150.

5. The transfer-resistant cosmetic composition according to claim 1 wherein, in which the siloxane based polyamide of formula I, n is a number between 1 and 500.

6. The transfer-resistant cosmetic composition according to claim 5 wherein n is a number between 1 and 100.

7. The transfer-resistant cosmetic composition according to claim 5 wherein n is a number between 4 and 25.

8. The transfer-resistant cosmetic composition according to claim 1 wherein X is a linear or branched chain alkylene having 1 to 30 carbons.

9. The transfer-resistant cosmetic composition according to claim 8 wherein X is a linear or branched chain alkylene having 3 to 10 carbons.

10. The transfer-resistant cosmetic composition according to claim 8 wherein X is a linear or branched chain alkylene having 10 carbons.

11. The transfer-resistant cosmetic composition according to claim 1 wherein Y is selected from the group consisting of linear or branched chain alkylenes having 1–40 carbons.

12. The transfer-resistant cosmetic composition according to claim 11 wherein Y is selected from the group consisting of linear or branched chain alkylenes having 1 to 20 carbons.

13. The transfer-resistant cosmetic composition according to claim 11 wherein Y is selected from the group consisting of linear or branched chain alkylenes having 2 to 6 carbons.

14. The transfer-resistant cosmetic composition according to claim 11 wherein Y is selected from the group consisting of linear or branched chain alkylenes having 6 carbons.

15. The transfer-resistant cosmetic composition according to claim 11 wherein Y is selected from the group consisting of linear or branched chain alkylenes having 1 to 20 carbons wherein:
 (a) the alkylene group may contain in the alkylene portion at least one of
  (i) 1 to 3 amide linkages or
  (ii) a $C_5$ or $C_6$ cycloalkane or
  (iii) a phenylene group optionally substituted by 1 to 3 members selected independently from the group consisting of $C_1$ to $C_3$ alkyls; and
 (b) the alkylene group may be substituted by at least one member selected from the group consisting of
  (i) a hydroxy;
  (ii) a $C_3$ to $C_8$ cycloalkane;
  (iii) 1 to 3 members selected independently from the group consisting of $C_1$ to $C_3$ alkyls, phenyl optionally substituted by 1 to 3 members selected independently from the group consisting of $C_1$ to $C_3$ alkyls;

(iv) $C_1$ to $C_3$ alkyl hydroxy; and (v) $C_1$ to $C_6$ alkyl amine.

16. The transfer-resistant cosmetic composition according to claim 11 wherein Y is $T(R^{20})(R^{21})(R^{22})$, where each of $R^{20}$, $R^{21}$ and $R^{22}$ are independently selected from the group consisting of linear and branched $C_1$ to $C_{10}$ alkylenes; and T is selected from the group consisting of CR, where R is selected from hydrogen, the group consisting of $R^1$, $R^2$, $R^3$ and $R^4$ wherein $R^1$, $R^2$, $R^3$ and $R^4$ are the same or different and may be selected from the group consisting of methyl, ethyl, propyl, isopropyl, a siloxane chain, and phenyl; and a trivalent atom selected from N, P and Al.

17. The transfer-resistant cosmetic composition comprising at least one siloxane based polyamide according to claim 1 wherein the molecular weight is between 100,000 and 140,000.

18. The transfer-resistant cosmetic composition according to claim 1 further comprising a film forming polymer.

19. The transfer-resistant cosmetic composition according to claim 18 wherein the film former is a silicone or a silicone derivative.

20. The transfer-resistant cosmetic composition according to claim 18 wherein the film forming polymer is selected from the group consisting of siloxysilicates and polydimethylsilsesquioxanes and their mixtures.

21. The transfer-resistant cosmetic composition according to claim 1 further containing an additive selected from the group consisting of pigments, antioxidants, fillers, thickeners, preservatives, fragrances, waxes, gums, resins, surfactants, emulsifiers, water, emollients, vitamins, essential fatty acids, sunscreens, sun filters and their mixtures.

22. The transfer-resistant cosmetic composition according to claim 1 wherein said cosmetic composition is a make up composition for keratinous substances such as skin, hair, eye lashes, eye brows, nails, lips.

23. The cosmetic composition according to claim 22 wherein said composition is selected from the group consisting of foundations, concealers, lipsticks, mascaras, and sunscreen compositions.

24. A method of structuring a liquid fatty phase in the presence of a non-silicone volatile oil, comprising adding a siloxane based polyamide to the liquid fatty phase, wherein the siloxane based polyamide is a polymer comprising multiples of a unit represented by the following formula (A):

Formula A

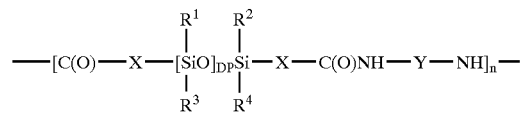

where:

(a) DP is between 1 and 700;

(b) n is a number selected from the group consisting of 1–500;

(c) X is a linear or branched chain alkylene having 1–30 carbons;

(d) Y is selected from the group consisting of linear or branched chain alkylenes having 1–40 carbons;

(d) $R^1$, $R^2$, $R^3$ and $R^4$ are the same or different and may be selected from the group consisting of methyl, ethyl, propyl, isopropyl, a siloxane chain, and phenyl, and wherein the liquid fatty phase comprises a volatile silicone oil is selected from the group consisting of octyltrimethicone, hexyltrimethicone, decamethylcyclopentasiloxane D5, octamethyl dyclotetrasiloxane D4, dodecamethyl cyclohexasiloxane D6, heptamethyl octyltrisiloxane, decamethyl tetrasiloxane, dodecamethyl pentasiloxane, polydimethylsiloxane at 1.5 centistokes (cSt), polydimethylsiloxane at 2 centistokes, polydimethylsiloxane at 3 centistokes, polydimethylsiloxane at 5 centistokes and their mixtures.

25. The transfer resistant cosmetic composition according to claim 1, wherein the degree of polymerization DP is 100.

* * * * *

UNITED STATES PATENT AND TRADEMARK OFFICE
CERTIFICATE OF CORRECTION

PATENT NO. : 6,958,155 B2  Page 1 of 1
APPLICATION NO. : 10/166762
DATED : October 25, 2005
INVENTOR(S) : Shao Xiang Lu et al.

It is certified that error appears in the above-identified patent and that said Letters Patent is hereby corrected as shown below:

Column 38, lines 22 & 23, "to claim 1 wherein, in which the siloxane based polyamide of formula I, n is a number between 1 and 500."

should read

--to claim 1 wherein n is a number between 1 and 500.--

Column 40, line 29, "dyclotetrasiloxane D4" should read --cyclotetrasiloxane D4--.

Signed and Sealed this

Twelfth Day of August, 2008

JON W. DUDAS
*Director of the United States Patent and Trademark Office*